US012728239B2

(12) United States Patent
Schulze

(10) Patent No.: US 12,728,239 B2
(45) Date of Patent: Sep. 8, 2026

(54) FLEXIBLE TUBULAR SPRING STRUCTURE, AND SCORING BALLOON CATHETER EQUIPPED THEREWITH

(71) Applicant: Nu-Life Consulting Pte Ltd, Singapore (SG)

(72) Inventor: John E. Schulze, Singapore (SG)

(73) Assignee: Nu-Life Consulting Pte Ltd, Singapore (SG)

(*) Notice: Subject to any disclaimer, the term of this patent is extended or adjusted under 35 U.S.C. 154(b) by 1000 days.

(21) Appl. No.: 17/520,693

(22) Filed: Nov. 7, 2021

(65) Prior Publication Data

US 2022/0054805 A1 Feb. 24, 2022

Related U.S. Application Data

(63) Continuation of application No. PCT/US2020/031743, filed on May 7, 2020.

(51) Int. Cl.

*A61M 25/10* (2013.01)
*A61B 17/00* (2006.01)

(Continued)

(52) U.S. Cl.

CPC ......... *A61M 25/1002* (2013.01); *A61B 17/22* (2013.01); *A61B 17/320725* (2013.01); *A61M 25/104* (2013.01); *A61B 2017/00778* (2013.01); *A61B 2017/00893* (2013.01); *A61B 2017/22001* (2013.01); *A61B 2017/22038* (2013.01);

(Continued)

(58) Field of Classification Search

CPC .............. A61M 25/10; A61M 25/1038; A61M 25/104; A61M 2025/1043; A61M 2025/1031; A61M 2025/109; A61B 17/22; A61B 2017/32096; A61B 2017/22051; A61B 2017/22077; A61B 2017/320725;

(Continued)

(56) References Cited

U.S. PATENT DOCUMENTS 4,273,128 A 6/1981 Lary
5,071,424 A 12/1991 Reger (Continued)

FOREIGN PATENT DOCUMENTS

WO WO2020144208 A1 7/2020

*Primary Examiner* — Michael J Tsai
*Assistant Examiner* — Forrest B Dipert

(57) ABSTRACT

A resiliently expandable elongate tubular spring structure, e.g., corresponding to a metal mesh type structure, mountable or mounted to a scoring balloon catheter includes multiple ring structures that are longitudinally separated from each other along portions of a balloon working region, and which are resiliently radially expandable in response to outwardly directed balloon expansion forces. Pairwise adjacent ring structures are structurally coupled and separated from each other by a scoring link, e.g., a single scoring link, configured as a traumatic structure with respect to vascular tissue, e.g., by way of having a square, trapezoidal, or raised blade tissue scoring/cutting profile. Each ring structure includes a pair of radially resiliently radially expandable annular springs, longitudinally separated from each other by a plurality of spacing elements, e.g., wire links, and which are atraumatic or substantially atraumatic structures relative to the scoring link with respect to tissue.

27 Claims, 17 Drawing Sheets

(51) Int. Cl.
*A61B 17/22* (2006.01)
*A61B 17/3207* (2006.01)

(52) U.S. Cl.
CPC ............... *A61B 2017/22061* (2013.01); *A61B 2017/22062* (2013.01); *A61M 2025/1004* (2013.01); *A61M 2025/1031* (2013.01); *A61M 2025/105* (2013.01); *A61M 2025/1086* (2013.01); *A61M 2025/109* (2013.01)

(58) Field of Classification Search
CPC ........... A61B 2017/22061; A61F 2/958; A61F 2002/8583; A61F 2002/9583
See application file for complete search history.

(56) References Cited

U.S. PATENT DOCUMENTS

| | | | | |
|---|---|---|---|---|
| 5,196,024 | A | 3/1993 | Barath | |
| 5,320,634 | A | 6/1994 | Vigil | |
| 5,616,149 | A | 4/1997 | Barath | |
| 5,797,935 | A | 8/1998 | Barath | |
| 6,036,708 | A | 3/2000 | VanSciver | |
| 6,165,187 | A | 12/2000 | Reger | |
| 7,131,981 | B2 | 11/2006 | Appling | |
| 8,398,662 | B2 | 3/2013 | Granada | |
| 8,613,721 | B2 | 12/2013 | Wulfman | |
| 9,011,896 | B2 | 4/2015 | Speck | |
| 9,173,977 | B2 | 11/2015 | AngioScore | |
| 9,763,691 | B2 | 9/2017 | Spencer | |
| 10,076,641 | B2 | 9/2018 | Konstantino et al. | |
| 10,166,374 | B2 | 1/2019 | Giasolli et al. | |
| 10,299,823 | B2 | 5/2019 | Piccagli | |
| 10,314,947 | B2 | 6/2019 | Speck | |
| 10,471,238 | B2 | 11/2019 | Schneider et al. | |
| 10,905,863 | B2 | 2/2021 | Giasolli et al. | |
| 11,083,571 | B2 * | 8/2021 | Manash | A61F 2/2418 |
| 2003/0040770 | A1 | 2/2003 | Radisch | |
| 2004/0143287 | A1 * | 7/2004 | Konstantino | A61B 17/320725 606/194 |
| 2004/0230293 | A1 | 11/2004 | Yip et al. | |
| 2005/0021071 | A1 | 1/2005 | Konstantino et al. | |
| 2005/0080478 | A1 * | 4/2005 | Barongan | A61F 2/86 623/1.36 |
| 2006/0085026 | A1 | 4/2006 | Appling | |
| 2006/0173487 | A1 | 8/2006 | Uflacker | |
| 2006/0178685 | A1 | 8/2006 | Melsheimer | |
| 2006/0184191 | A1 | 8/2006 | O'Brian | |
| 2006/0259005 | A1 * | 11/2006 | Konstantino | A61P 9/10 623/1.42 |
| 2007/0213761 | A1 | 9/2007 | Murphy et al. | |
| 2009/0105687 | A1 | 4/2009 | Deckman | |
| 2009/0306582 | A1 | 12/2009 | Granada et al. | |
| 2010/0241148 | A1 | 9/2010 | Schon et al. | |
| 2011/0152905 | A1 * | 6/2011 | Eaton | A61M 25/104 606/159 |
| 2012/0232505 | A1 * | 9/2012 | Eskaros | A61F 5/445 604/335 |
| 2013/0041391 | A1 | 2/2013 | Spencer et al. | |
| 2014/0257181 | A1 | 9/2014 | Speck | |
| 2015/0216552 | A1 | 8/2015 | Hefer | |
| 2016/0324538 | A1 | 11/2016 | Schneider | |
| 2017/0105758 | A1 | 4/2017 | Piccagli | |
| 2018/0036032 | A1 | 2/2018 | Spencer et al. | |
| 2018/0289517 | A1 | 10/2018 | Jimenez et al. | |

* cited by examiner

FLEXIBLE TUBULAR SPRING STRUCTURE, AND SCORING BALLOON CATHETER EQUIPPED THEREWITH

CROSS-REFERENCE TO RELATED APPLICATIONS

This application is a continuation of International Application No. PCT/US2020/031743, filed on 7 May 2020, which claims priority to (a) U.S. Provisional Application No. 62/344,603, filed on 7 May 2019; and (b) U.S. Provisional Application No. 62/848,387, filed on 15 May 2019. Each of International Application No. PCT/US2020/031743, U.S. Provisional Application No. 62/344,603, and U.S. Provisional Application No. 62/848,387 is incorporated herein by reference in its entirety.

TECHNICAL FIELD

Aspects of the present disclosure are directed to an elongate flexible tubular spring structure, and a scoring balloon catheter device that carries the flexible tubular spring structure. The flexible tubular spring structure includes a plurality of annular ring structures; and indexed longitudinal elements, including scoring elements, which couple annular ring structures in particular manners.

BACKGROUND

Cutting balloons and scoring catheters are often used to treat difficult-o-expand portions of vascular lesions, e.g., in a manner indicated in FIG. 1, during angioplasty procedures. Such devices, when properly designed and applied can produce multiple linear and/or curved grooves or cuts in the lesion surface. Upon expansion of a scoring catheter's balloon (if so equipped) or upon further expansion of the lesion via an angioplasty balloon, these grooves or cuts can act as foci for controlled circumferential tissue dissection and plaque separation, thus allowing the lesion to separate into multiple lobes using reduced mechanical force, as compared to the effects of balloon angioplasty alone as shown in FIG. 2A.

Thus, cutting balloons and devices that achieve a similar effect facilitate an improved lesion compliance and a larger post procedural lumen diameter, while reducing vessel wall injury. For angioplasty treatments that further involve application of a therapeutic substance, properly controlled dissection of difficult to expand lesions prior to application of the therapeutic substance to the vessel wall is important to allow the therapeutic substance to pass through the calcium and plaque in the channels created by the cutting balloon in order to easily diffuse into the tissues of the underlying vessel wall.

As is known, Drug Coated Balloons (DCB's) are often used in the later parts of angioplasty procedures (after plain old balloon angioplasty (POBA) and/or scoring) to apply an anti-restenotic drug to the expanded lesion. Adequate expansion of the lesion, which creates channels through the lesion, is vital to the effective entry of the anti-restenotic drug into the underlying media and adventitia, so that effectiveness of the drug treatment can be assured.

SUMMARY

Technical Problem(s)

FIG. 2B shows longitudinal vascular tissue cuts created by the surgical blades of a Flextome™ Cutting Balloon™

(Boston Scientific Corporation, Marlborough, Massachusetts, USA). Particular physical aspects of the Flextome™ Cutting Balloon™ are shown in FIG. 3A. Because longitudinal steel blades are rigidly adhered to the balloon, this device, while conventionally considered the most effective, is not sufficiently flexible and is unable to reach and treat very tortuous lesions. FIG. 3B illustrates structural aspects of an AngioSculpt scoring balloon (Koninklijke Philips N.V., Amsterdam, Netherlands). Upon expansion, this device is claimed to create spiral grooves in the lesion. In one embodiment, the AngioSculpt device can be coated with a therapeutic substance, for example an antirestenotic drug. However, spiral dissections can more easily become uncontrolled as the scoring balloon expands, i.e., straight grooves or cuts as provided by the Flextome™ Cutting Balloon™ may generally be preferred because they may be more effective and/or safer.

The Bard Ultrascore™ Scoring Catheter (Bard Peripheral Vascular, Inc., Tempe, Arizona USA) shown in FIG. 4 places two straight 0.010" diameter longitudinal wires located circumferentially 150° apart along the length of an angioplasty balloon, which allows the grooves created by the device to be longitudinal, but only two grooves (180° apart) can be created per balloon expansion. However, it is desirable to have more than two grooves created per balloon expansion.

The FLEX Scoring Catheter® (VentureMed Group, Ltd., Columbus, Ohio USA) shown in FIG. 5 deploys three 0.010" atherotomes mounted on opposing leaf springs which can create longitudinal cuts along the lesion as the catheter is advanced and subsequently retracted. Additional cuts can be obtained by repeatedly advancing and retracting the catheter across the lesion, but the circumferential spacing of the cuts is difficult to control. A further disadvantage of this device is that there is no integral angioplasty balloon, and the lesion must be subsequently expanded by inserting a second POBA balloon catheter into the lesion.

U.S. Pat. No. 9,375,328 describes an expandable and retractable "non-deployable" stent loosely in contact with the outer surface of an angioplasty balloon. The longitudinal elements of the stent which are used for scoring run the entire length of the balloon and are secured both proximally and distally of the angioplasty balloon to the catheter shaft. Since the wires are attached to the catheter shaft and only loosely associated with the folded balloon during insertion and delivery and removal of the device into and out of the lesion, and the longitudinal elements are further designed to stretch to accommodate the expansion of the balloon, there is danger of entanglement of these long longitudinal wires with other devices being used to treat the vessel, for example guidewires and other implanted stents.

U.S. Pat. No. 8,348,987 describes a scoring structure for a balloon, which provides expandable circumferential members connected by longitudinal cutting members. Unfortunately, the scoring efficacy of this scoring structure is undesirably limited or low, e.g., particularly for large(r) or thick(er) lesions, as the structural organization of the longitudinal cutting members relative to the expandable circumferential members limits the effectiveness and/or extent of force transfer from the radial expansion of the balloon to cutting forces along the longitudinal cutting members.

US20110238154 describes an intravascular treatment device having a mesh portion with protuberance bearing treatment implements carried thereby, as well as protective elements that shield intravascular tissues from the protuberance bearing treatment implements during deployment. Unfortunately, the structural configuration of the treatment device of US20110238154 limits or restricts device flexibility, rendering the device unsuitable for the treatment of lesions in highly tortuous vascular pathways. Moreover, the protective elements render the device needlessly complex.

Technical Solution(s)

In accordance with various embodiments of the present disclosure, a scoring balloon catheter and/or a tubular spring structure thereof or therefor, e.g., a tubular mesh structure, is configured for creating circumferentially evenly spaced cuts or grooves in an atherosclerotic lesion as part of an angioplasty treatment, e.g., longitudinal cuts or grooves with respect to a central axis of the vessel in which the lesion resides, and/or a central axis of the lesion itself.

In the tubular spring structure, structural elements, which are typically longitudinal scoring or cutting elements, are configured for creating at least 3 cuts or grooves, and typically 4-5 cuts or grooves, e.g., evenly spaced around the circumference of the lesion, to obtain smaller, more uniform lobes upon expansion for a less traumatic treatment effect. Hence, in various embodiments, a scoring balloon catheter and/or tubular spring structure thereof or therefor is configured to provide at least 3 (and typically 5) cuts or grooves, e.g., longitudinal cuts or grooves, in the lesion while remaining flexible enough when mounted on an angioplasty balloon to be delivered to tortuous vessels. Longitudinal scoring or cutting elements we provided as part of the tubular spring structure. To maximize the flexibility of the tubular spring structure or the balloon catheter on which it is mounted, annular band structures or bands are provided along the tubular spring structure's length, where the annular bands are separated by spatial gaps. Any given individual longitudinal cutting element does not span the entire length of the tubular spring structure or the entire working region or working length of the balloon, but rather couples, extends between, or connects only two serially or directly successive or pairwise adjacent annular bands of the tubular spring structure.

To reduce procedure time and cost, the ability to expand the lesion with the scoring catheter is typically an integral part of the action of the scoring catheter.

To further reduce cost and time, at least one type of coating can optionally be provided on portions of the tubular spring structure, e.g., portions of the mesh thereof, for concurrent delivery of therapeutic substance treatment of the lesion without the need for insertion of an additional device to deliver the therapeutic substance(s).

Optionally, enhanced entry of the therapeutic substance into the vessel wall can be facilitated or effectuated by placing at least one therapeutic substance coating on at least the longitudinal cutting or scoring elements of the tubular spring structure, where the therapeutic substance(s) can travel into the vessel wall along the dissection channels created by the scoring catheter.

These and other aspects of the present disclosure we further described below.

In general, a scoring catheter in accordance with various embodiments of the present disclosure provides an easily insertable or inserted but removable tubular spring structure, e.g., as a mesh structure such as a metal mesh, employing short (e.g., lengthwise short) annular ring structures or rings which integrally carry multiple indexed longitudinal elements that couple or interconnect pairs (e.g., adjacent pairs) of rings. More particularly, the longitudinal elements are radially or circumferentially indexed about the circumference of the tubular spring structure and/or scoring catheter, e.g., separated by a predetermined number of degrees from each other relative to a cross-section of the scoring catheter through a lengthwise or longitudinal axis thereof. The longitudinal elements provide for lower pressure expansion, and controlled injury in calcified vessels upon device expansion. First, shorter, or short longitudinal elements couple or connect annular springs of each ring; and second, longer, or long longitudinal elements, which carry or form therapeutic elements, e.g., indexed longitudinal scoring/cutting elements or structures, couple or connect pairs of adjacent rings. There is typically no requirement for protection of vascular tissue from the therapeutic elements during scoring catheter delivery, because the mesh pattern can be in direct contact with the vessel wall during scoring catheter delivery without causing excessive injury. In multiple embodiments, protective elements for limiting or shielding the vessel wall or vascular tissues from exposure to the indexed longitudinal scoring/cutting elements during scoring catheter delivery are excluded, e.g., entirely excluded.

In various embodiments, the scoring catheter includes a tubular spring structure, which typically includes or is formed as a metal mesh, and which is slightly radially expanded from a resting state to be circumferentially mounted upon, and to grip firmly to a folded angioplasty balloon portion of an angioplasty catheter. The tubular spring structure includes or is formed as a series of band or ring structures or rings (e.g., at least two rings, or three or more rings, such as at least four rings) that are separated from each other, and which are disposable or disposed or arrayed along portions of the length of the folded balloon, each ring biased to exert compressive or constrictive force and grip firmly to the folded balloon prior to use. Each ring includes first, shorter, or short wire spacing elements therein or therealong, which are typically circumferentially disposed about the ring. Second, longer, or long wire structures or links, which carry or are formed as scoring/cutting structures, which are selectively circumferentially disposed at predetermined spatial locations or intervals about pairwise adjacent rings, structurally couple or interconnect and maintain the longitudinal spacing between the rings. In multiple embodiments, at least some or all wire structures, links, and/or elements of the tubular spring structure can be approximately longitudinal or linear elements when the scoring catheter or the tubular spring structure exists in a straight configuration, e.g., with respect to a central axis of the tubular spring structure, the balloon, and/or the scoring catheter, however, in a number of embodiments, one or more wire structures, links, and/or elements can be curved elements, e.g., geometrically corresponding to one or more spiral shapes or geometries.

Each ring has multiple springs, e.g., a pair of longitudinally separated springs, formed of spring members, e.g., c-shaped or v-shaped spring members, adapted to expand the rings to a substantially larger diameter through elastic deformation of the springs in the ring structure (with minimal or negligible plastic deformation) upon or in response to inflation of the angioplasty balloon. The scoring catheter is adapted to be inserted into a vessel within the vascular system using known angioplasty techniques. Upon accessing or crossing a lesion to be treated, the balloon is expanded to provide radial contact, e.g., forceful radial contact, of at least particular portions of the tubular spring structure with or against the lesion. More particularly, in an expanded configuration, the scoring/cutting links or structures of the tubular spring structure create grooves or cuts in the lesion, which are circumferentially spaced apart from each other with respect to the peripheries of the rings, or analogously or equivalently, with respect to the circumference of the vessel. At least some or all of the grooves or cuts are in a longitudinal direction, e.g., along the length or essentially parallel to a central axis of the vessel and/or the central or longitudinal axis of the rings, the balloon, and the scoring catheter.

Upon further expansion of the balloon, controlled dissections along the loci of the longitudinal or linear elements of the tubular spring structure are created. Upon deflation of the balloon, the tubular spring structure contracts around the balloon and is removed from the body along with the catheter body and balloon. In an optional embodiment, the tubular spring structure includes one or more tethers (e.g., a single tether, or a pair of tethers), and a ring collar is attached to each tether as well as the catheter shaft proximal to the angioplasty balloon to prevent slippage of the tubular spring structure during balloon expansion and catheter use. In another optional embodiment, portions of the tubular spring structure may carry or include a therapeutic drug substance, e.g., at least along some of the longitudinal elements of the tubular spring structure, such as the scoring/cutting elements.

Non-limiting representative examples in accordance with particular embodiments of the present disclosure are detailed herein.

In accordance with an aspect of the present disclosure, a flexible elongate tubular spring structure for or carried by a flexible scoring balloon catheter is configured for insertion into a vessel within a mammalian (e.g., living mammalian) vascular system, or other anatomic fluid or air carrying conduit or duct within a mammalian (e.g., living mammalian) body. The scoring balloon catheter includes or consists essentially of an inflatable elongate balloon having a working region spanning a length, an outer surface along its working region, a first internal passage along which a guide wire is insertable, a second internal passage for passage of a pressurized fluid in communication with the interior of the balloon (commonly described as a "balloon expansion lumen"), and a first longitudinal axis centrally aligned with and extending through the first internal passage, wherein the working region of the balloon in a folded, undeployed, or unexpanded state respectively has a folded, undeployed, or unexpanded outer cross sectional area perpendicular to the first longitudinal axis, wherein the working region of the balloon in an expanded or deployed state respectively has an expanded or deployed outer cross sectional area perpendicular to the first longitudinal axis that is greater than the folded outer cross sectional area, the undeployed outer cross sectional area, and the unexpanded cross sectional area. The tubular spring structure has a distal end, a proximal end, a length therebetween within which a lumen resides, and a second longitudinal axis centrally aligned with its lumen, and wherein the tubular spring structure includes or consists essentially of:

(i) a plurality of annular ring structures, each annular ring structure having an unexpanded length and providing along its length a lumen having a central axis longitudinally extending therethrough and a relaxed cross sectional area perpendicular to the central axis which in the absence of the balloon is less than the folded, undeployed, or unexpanded outer cross sectional area of the balloon's working region, wherein each annular ring structure is configured for circumferential engagement with the outer surface of the balloon such that the central axis of the annular ring structure is longitudinally aligned with a portion of the first longitudinal axis, wherein each annular ring structure is configured for resilient expansion in radial directions perpendicular to the central axis including outward radial expansion away from the central axis in response to radial forces exerted on the annular ring structure by the expansion of the balloon, and wherein each annular ring structure comprises or consists essentially of:
  - a distal annular spring having a circumference and configured for circumferentially residing around the outer surface of the balloon, wherein the distal annular spring is configured for resilient radial expansion relative to a plane perpendicular to the central axis, and wherein the distal annular spring is configured for exerting an inward circumferential compressive force toward the central axis in response to outward radial expansion of the distal annular spring away from the central axis beyond the relaxed cross sectional area;
  - a proximal annular spring longitudinally separated from the distal annular spring, the proximal annular spring having circumference and configured for circumferentially residing around the outer surface of the balloon, wherein the proximal annular spring is configured for resilient radial expansion relative to a plane perpendicular to the central axis, and wherein the proximal annular spring is configured for exerting an inward circumferential compressive force toward the central axis in response to outward radial expansion of the proximal annular spring away from the central axis beyond the relaxed cross sectional area;
  - a set of spacing elements peripherally disposed around the annular ring structure between the distal annular spring and the proximal annular spring, wherein the set of spacing elements couples the distal annular spring to the proximal annular spring and maintains a longitudinal separation distance between the distal and proximal springs (e.g., corresponding to the unexpanded and/or expanded length of the annular ring structure); and (ii) a plurality of scoring links, wherein each scoring link has a length and couples a distinct pair of adjacent annular ring structures and spans a longitudinal spatial gap between each annular ring structure within the pair of annular ring structures coupled thereby, wherein each scoring link comprises a set of scoring structures along at least portions of its length, wherein each scoring structure is configured as atraumatic element with respect to contact with tissue within the vessel, conduit, or duct, wherein serially successive scoring links along the length of the tubular spring structure are disposed at or indexed across different radial positions relative to each other about the second longitudinal axis, and wherein the length of each scoring link is greater than the unexpanded length of each annular ring structure within the adjacent pair of annular ring structures coupled thereby.

Particular embodiments can be further characterized by one or more of the following, either individually or in combination:

Each of the distal annular spring and the proximal annular spring has a cross sectional area perpendicular to the central axis which in the absence of the balloon is less than the folded, undeployed, or unexpanded outer cross sectional area of the balloon.

Each scoring link can have a length greater than 200% of the unexpanded length of a shortest annular ring structure within the pair of adjacent annular ring structures coupled thereby.

For each pair of adjacent annular ring structures, the spatial gap between the annular ring structures thereof can be at least 0.3 mm.

Each pair of adjacent annular ring structures is longitudinally organized as a first annular ring structure disposed distal to a second annular ring structure, wherein the proximal annular spring of the first annular ring structure is closest to the distal annular spring of the second annular ring structure, and wherein the scoring link that couples the first annular ring structure to the second annular ring structure extends from the distal annular spring of the first annular ring structure to the proximal annular spring of the second annular ring structure.

Each spacing element is configured as a generally atraumatic element with respect to contact with tissue within the vessel, conduit, or duct.

Each spacing element can have a width that is between 50% to 500% of the width of each scoring link and/or a scoring element carried thereby.

For each annular ring structure, the set of spacing elements includes a plurality of distinct spacing elements longitudinally aligned with the central axis, wherein the tubular spring structure has a total of N scoring links and (N+1) annular ring structures. An angular separation between serially successive scoring links around the second longitudinal axis is (360/Y) degrees, where Y is typically a number between 3 and 5. In some (though not necessarily all) embodiments, Y is equal to N.

The distal annular spring includes or consists essentially of a plurality of spring members that are coupled together around the circumference of the distal annular spring. The proximal annular spring includes or consists essentially of a plurality of spring members that are coupled together around the circumference of the proximal annular spring.

Each spring member can include a first end segment, a second end segment, and an apex therebetween, and wherein each end segment of each spring member is coupled to one of either a spacing element or a scoring link. Each spring member can include or be in the form of a geometric shape resembling, approximating, or essentially identical to a “v” or a “c”.

The second longitudinal axis adopts a curvilinear or curved (e.g., “s” type) shape in response to flexure of the tubular spring structure, and each scoring link has a geometric shape that is essentially identical to the geometric shape of a segment along or of the second longitudinal axis to which it most closely resides in response to flexure of the tubular spring structure.

Each scoring structure within the set of scoring structures is elongate and is longitudinally aligned relative to the second longitudinal axis.

Each scoring link has a scoring structure integrally formed thereon, or integrally forms a scoring structure. In several embodiments, each scoring structure can have a rectangular, trapezoidal, or raised blade cross-sectional shape perpendicular to the second longitudinal axis.

In multiple embodiments, each spacing element within each annular ring structure of a pair of adjacent annular ring structures is elongate and is longitudinally aligned with the central axis, and each spacing element within each annular ring structure of the pair of adjacent annular ring structures has a length that is at least 40% of the length of the scoring link that couples the adjacent pair of annular ring structures.

Each annular ring structure can include or consist essentially of a metal mesh. The tubular spring structure can be formed of at least one metal. The tubular spring structure can integrally be formed from a metal tube.

At least portions of at least some of the plurality of scoring links of the tubular spring structure and/or one or more other portions of the tubular spring structure can carry at least one therapeutic substance. In some embodiments, the at least one therapeutic substance is carried only by the scoring links.

In accordance with an aspect of the present disclosure, a scoring balloon catheter structure includes: an elongate angioplasty balloon having a first length, a periphery, and a working region along its length; and an elongate expandable tubular mesh structure mounted on the angioplasty balloon and having a second length, wherein the second length is parallel to the first length when the angioplasty balloon and the expandable tubular mesh structure are in a straight configuration, wherein the expandable tubular mesh structure includes a plurality of ring structures that circumferentially surround the angioplasty balloon along its working region, wherein each ring structure has a third length and comprises a pair of distinct resiliently expandable rings (e.g., a first or distal ring/spring and a second or proximal ring/spring) lengthwise coupled by a set of spacing elements, wherein each ring structure is configured for elastic expansion and deformation in response to expansion of the angioplasty balloon while remaining below its plastic deformation limit, wherein each ring structure is separated from an adjacent ring structure along the second length by a nonzero first separation distance, wherein each distinct pair of adjacent ring structures is coupled by a set of scoring elements, e.g., a single distinct scoring element, having a fourth length that is greater than the third length (e.g., in several embodiments the fourth length is approximately equal or equal to the first separation distance plus twice the third length) and which comprises a traumatic structure configured for scoring or cutting tissue within a mammalian (e.g., living mammalian) anatomic fluid or air carrying vessel, conduit, or duct. The set of spacing elements is substantially atraumatic, essentially atraumatic, or atraumatic relative to the scoring element(s) with respect to tissue within the mammalian vessel, conduit, or duct. The scoring balloon catheter structure can omit or exclude, and in various (though not necessarily all) embodiments does exclude, protective elements configured to limit or shield contact between each scoring element and tissue within the vessel, conduit, or duct prior to inflation of the balloon from a folded, undeployed, or unexpanded state to an expanded or deployed state.

Each ring structure is slightly expanded beyond a resting state when the angioplasty balloon is in a folded, undeployed, or unexpanded state.

Each scoring element can exhibit one of a square, a trapezoidal, and a raised blade cross sectional profile.

A therapeutic substance coating can be disposed on at least a portion of the tubular mesh structure, for instance, on each scoring element.

The tubular mesh structure can include at least four ring structures, and at least three scoring elements that are circumferentially separated from each other at indexed positions about the periphery of the angioplasty balloon.

Each ring structure can include a pair of annular spring structures or springs that are coupled together by a plurality of spacing elements that establish a nonzero second separation distance between the pair annular spring structures. The plurality of spacing elements are atraumatic relative to each scoring element with respect to vascular tissue and/or tissue(s) forming the lining(s) of other mammalian (e.g., living mammalian) conduits or ducts, e.g., each spacing element is formed as an atraumatic, substantially atraumatic, or not intentionally traumatic structure.

In accordance with an aspect of the present disclosure, a flexible scoring balloon catheter structure or flexible scoring balloon catheter includes or consists essentially of:

an inflatable elongate balloon having a distal end, a proximal end, and a working region therebetween configured for dilation within a vessel of a mammalian (e.g., living mammalian) cardiovascular system or other fluid or air carrying conduit or duct within a mammalian (e.g., living mammalian) body, the balloon having a length along its working region, an outer surface along its working region, an internal passage along which a guide wire is insertable, and a first longitudinal axis centrally aligned with and extending through the internal passage, wherein the working region of the balloon in a folded or undeployed state respectively has a folded or undeployed outer cross sectional area perpendicular to the first longitudinal axis, and wherein the working region of the balloon in an expanded or deployed state respectively has an expanded or deployed outer cross sectional area perpendicular to the first longitudinal axis that is greater than the folded outer cross sectional area and the undeployed outer cross sectional area;

a catheter having a distal portion and a proximal portion, wherein the balloon is mounted on the catheter distal portion, and wherein the catheter comprises an inflation lumen extending therethrough in fluid communication with an interior region of the balloon; and a flexible elongate tubular spring structure as described herein (e.g., as described above), which surrounds portions of the working region of the balloon along the catheter distal portion.

The flexible scoring balloon catheter can further include at least one of:

(a) a tether structure configured for tethering or anchoring the tubular spring structure to at least one of (i) a portion of the catheter and (ii) a portion of the balloon, where the tether structure can include or consist essentially of: a tubular collar carried by a shaft of the catheter proximal to the balloon; and at least one elongate tether link (e.g., a single tether link, or a pair of tether links) coupled to each of the tubular collar and the tubular spring structure; (b) a proximal adhesive bond coupling a proximal end of the tubular spring structure to at least one of a proximal zone of the catheter distal portion and an unexpandable proximal segment of the balloon; and (c) a distal adhesive bond coupling a distal end of the tubular spring structure to at least one of a distal zone of the catheter distal portion and an unexpandable distal segment of the balloon. In an embodiment in which the flexible scoring balloon catheter includes each of the proximal adhesive bond and the distal adhesive bond, the distal adhesive bond can be intentionally formed weaker than the proximal adhesive bond, e.g., such that the distal adhesive bond breaks in response to expansion or inflation of the balloon.

The flexible scoring balloon catheter can omit or exclude, and in various (though not necessarily all) embodiments does exclude, protective elements configured to limit or shield contact between the plurality of scoring links and tissue within the vessel, conduit, or duct prior to inflation of the balloon from the folded, undeployed, or unexpanded state to the expanded or deployed state.

DETAILED DESCRIPTION OF PARTICULAR EMBODIMENTS

Herein, unless the context stipulates or requires otherwise, any use of the word "comprise," and variations such as "comprises" and "comprising," imply the inclusion of a stated element or step or group of elements or steps but not the exclusion of any other element or step or group of elements or steps.

The reference herein to any prior publication (or information derived from it), or to any matter which is known, is not, and should not be taken as an acknowledgment or admission or any form of suggestion that such prior publication (or information derived from it) or known matter forms part of the common general knowledge in the field of endeavor to which this specification relates.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in An Introduction to Mathematical Reasoning: Numbers, Sets, and Functions, "Chapter 11: Properties of Finite Sets" (e.g., as indicated on p. 140), by Peter J. Eccles, Cambridge University Press (1998)). Thus, a set includes at least one element. In general, an element of a set can include or be one or more portions of a structure, an object, a process, a composition, a physical parameter, or a value depending upon the type of set under consideration.

Herein, reference to one or more embodiments, e.g., as various embodiments, many embodiments, several embodiments, multiple embodiments, some embodiments, certain embodiments, particular embodiments, specific embodiments, or a number of embodiments, need not or does not mean or imply all embodiments.

FIGS. 7A-12B included herewith show aspects of non-limiting representative embodiments in accordance with the present disclosure, and particular structures or features shown in the FIGs. herein may not be shown to scale or precisely to scale relative to each other. The depiction of a given element or consideration or use of a particular element number in a particular FIG. or a reference thereto in corresponding descriptive material can encompass the same, an equivalent, an analogous, categorically analogous, or similar element or element number identified in another FIG. or descriptive material associated therewith. The presence of "/" in a FIG. or text herein is understood to mean "and/or" unless otherwise indicated. The recitation of a particular numerical value or value range herein is understood to include or be a recitation of an approximate numerical value or value range, for instance, within +/−20%, +/−15%, +/−10%, +/−5%, +/−2.5%, +/−2%, +/−1%, +/−0.5%, or +/−0%. The term "essentially all" can indicate a percentage greater than or equal to 90° %, for instance, 92.5%, 95%, 97.5%, 98%, 98.5%, 99%, 99.5%, or 100%.

Figure 1:
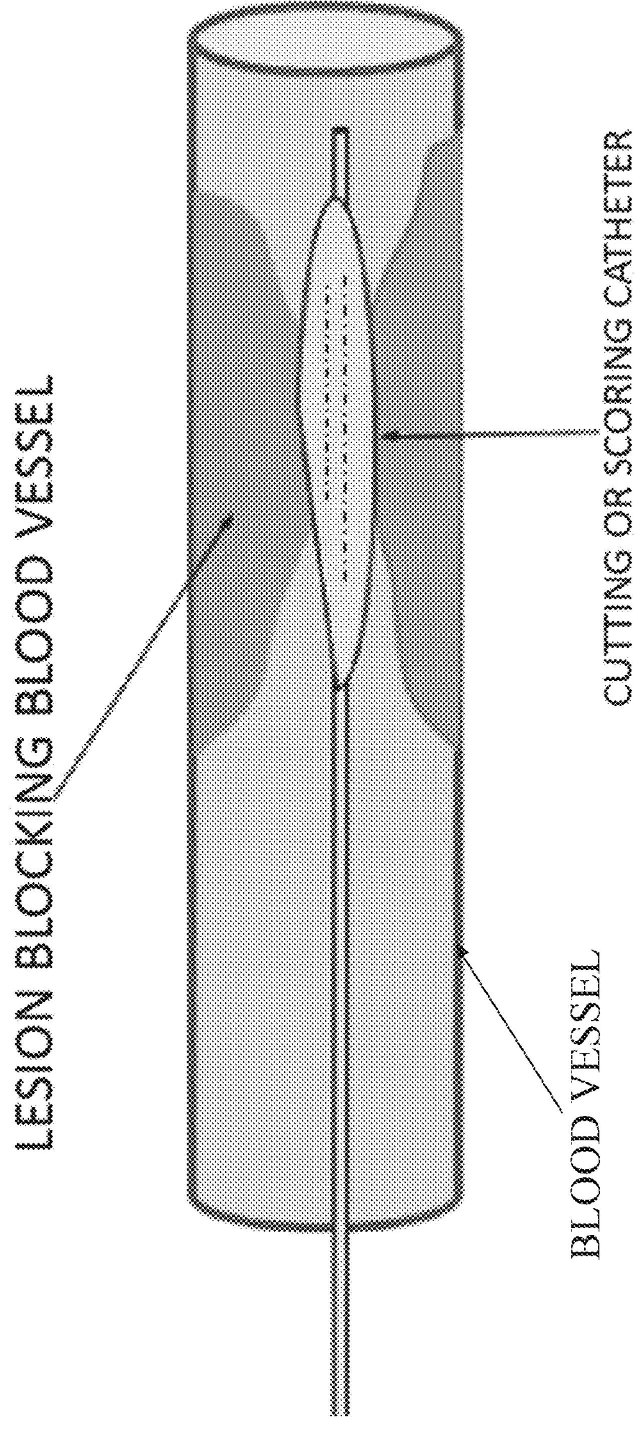
FIG. 1 illustrates general aspects of intravascular lesion treatment by way of a scoring balloon catheter.
Figures 2A, 2B:
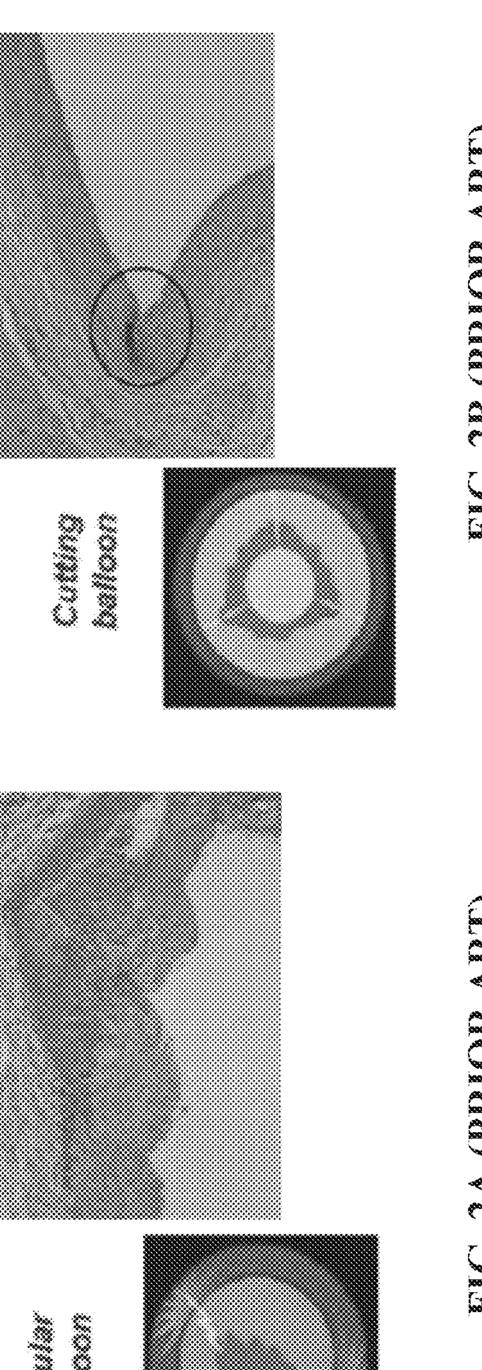
FIGS. 2A and 2B respectively illustrate vascular effects produced by balloon angioplasty alone, and longitudinal cuts created by a scoring balloon catheter such as a conventional Flextome™ Cutting Balloon™ (Boston Scientific Corporation, Marlborough, Massachusetts, USA).
Figures 3A, 3B:
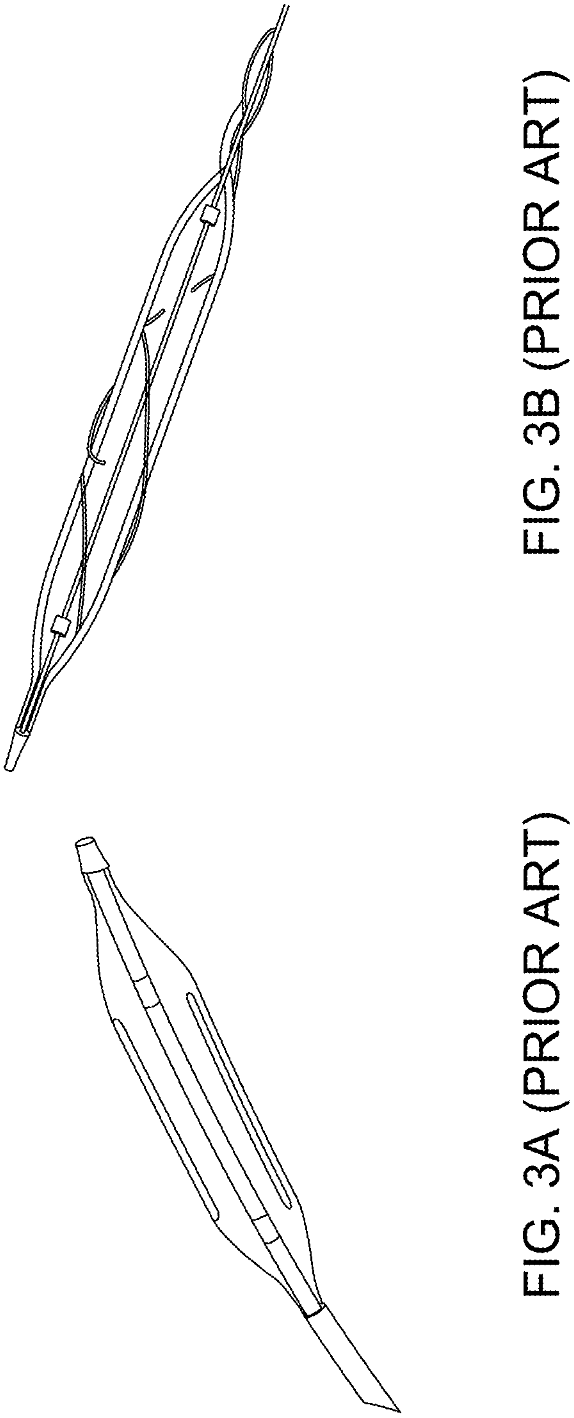
FIGS. 3A and 3B respectively illustrate structural aspects of a conventional Flextome™ Cutting Balloon™, and structural aspects of a conventional AngioSculpt scoring balloon (Koninklijke Philips N.V., Amsterdam, Netherlands).
Figure 4:
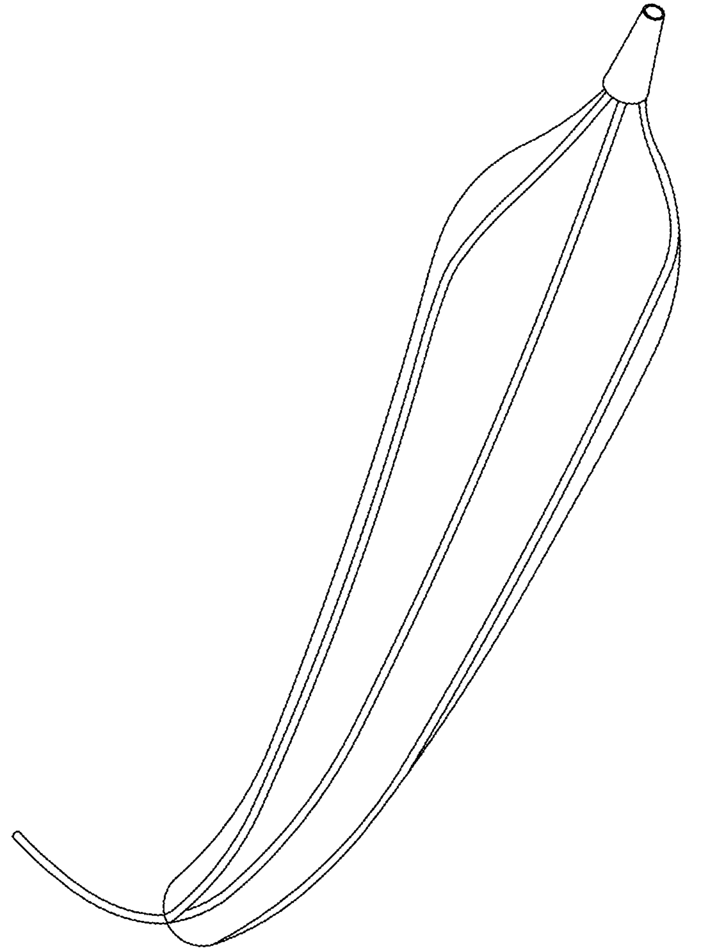
FIG. 4 illustrates aspects of a conventional Bard Ultrascore™ Scoring Catheter (Bard Peripheral Vascular, Inc., Tempe, Arizona USA).
Figure 5:
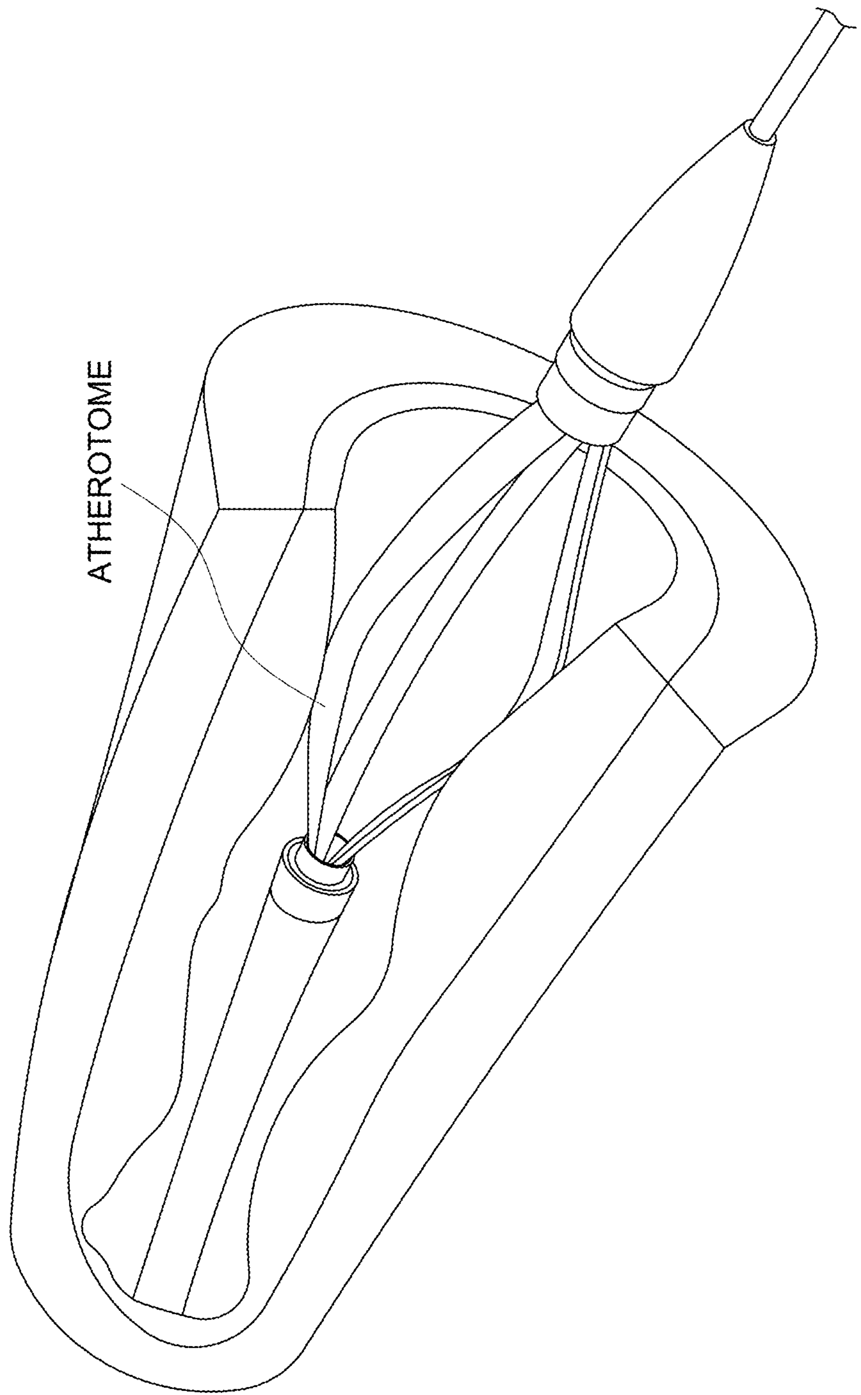
FIG. 5 illustrates aspects of a conventional FLEX Scoring Catheter® (VentureMed Group, Ltd., Columbus, Ohio USA).
Figures 6A, 6B:
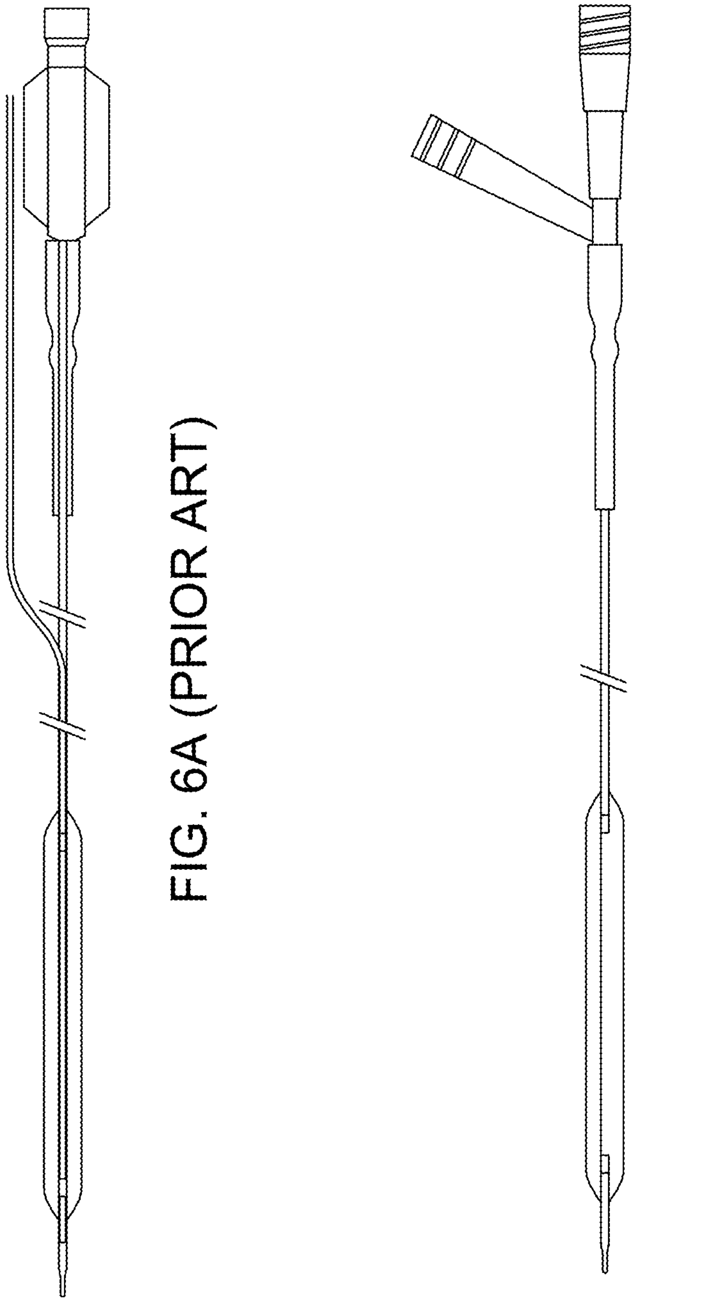
FIGS. 6A and 6B shows general structural aspects of particular types of conventional balloon angioplasty catheters.

FIGS. 6A and 6B illustrates general structural aspects of balloon angioplasty catheters, which will be readily understood by individuals having ordinary skill in the relevant art. More particularly, FIG. 6A illustrates a rapid exchange (RX) balloon angioplasty catheter; and FIG. 6B illustrates an over-the-wire (OTW) balloon angioplasty catheter.

Various embodiments in accordance with the present disclosure are directed to a tubular spring structure that is mountable or mounted on the balloon of a balloon angioplasty catheter to thereby form a scoring balloon catheter. More particularly, embodiments in accordance with the present disclosure are directed to an elongate tubular spring structure for a scoring balloon catheter, which is mountable or mounted to an angioplasty balloon (which can be referred to hereafter "balloon" for purpose of brevity and simplicity) thereof, and which carries scoring links and/or structures thereon. The balloon and the tubular spring structure carried thereby are deployable or positionable within a vessel or conduit of a mammalian vascular system or mammalian fluid carrying passage or duct. For use within the cardiovascular system, the following describes a representative or typical use scenario: After the balloon carrying the tubular spring structure is deployed or positioned at an intended or target site within the vessel, e.g., a vascular location at which intravascular tissue such as an atherosclerotic lesion resides, in association with expansion of the balloon followed by displacement of the balloon and the tubular spring structure carried thereby along a central or longitudinal axis of the vessel, the scoring links and/or scoring structures can contact and score or form grooves and/or cuts, e.g., longitudinal grooves/cuts, in the intravascular tissue at or along the target site. The tubular spring structure is configured or structurally organized or formed such that it is (a) highly flexible, bendable, conformable, or contortable in directions that radially extend away from a longitudinal axis thereof e.g., in essentially any direction in a plane perpendicular to its longitudinal axis, and is thus suitable for deployment and use in or along tortuous or highly tortuous vascular pathways; and (b) highly effective with respect to communicating, directing, or concentrating outward or radial balloon expansion forces to the scoring structures, and it is thus an effective or very effective scoring/cutting device. Aspects of non-limiting representative embodiments in accordance with the present disclosure are described in detail hereafter.

Figure 7A:
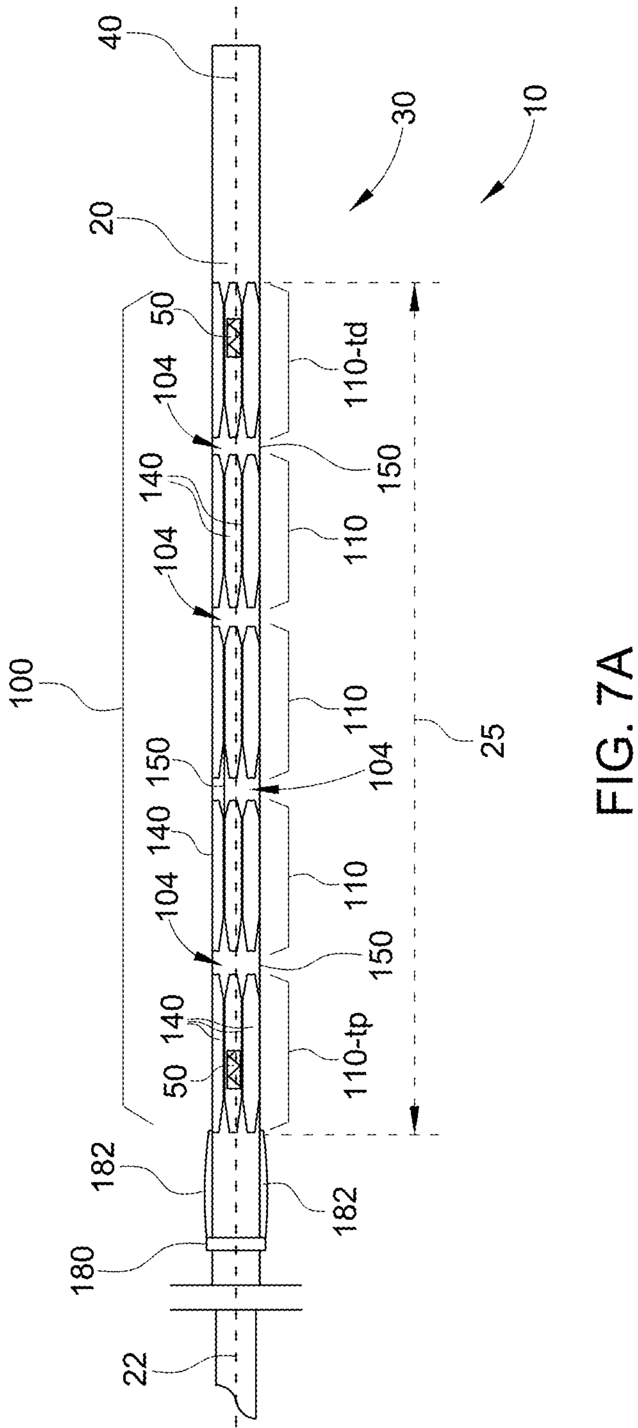
FIG. 7A is a side view showing an angioplasty balloon catheter or scoring balloon catheter carrying a tubular spring structure in accordance with an embodiment of the present disclosure.

FIG. 7A shows a distal portion or distal end of a balloon angioplasty catheter or scoring balloon catheter 10 in accordance with various embodiments of the present disclosure, illustrating an elongate angioplasty balloon portion or balloon 20 folded around the distal end of a catheter 30, and illustrating a distal tip of the catheter 30, and marker bands 50 mounted to an inner lumen of the catheter 30. Inserted inside the catheter inner lumen is a slideable guidewire 40, which is first inserted into the lesion area or lesion and which allows the catheter 30 to track over the guidewire into the area of the lesion, as is well known in the art of angioplasty treatments.

As will be readily understood by individuals having ordinary skill in the relevant art, the balloon 20 includes a working or treatment region 25 spanning a length; an outer surface along its working region 25; an internal passage along which the guidewire 40 is insertable; and a first lengthwise or longitudinal axis 22 that is centrally aligned with and which extends through its internal passage. When the balloon 20 is in a folded, undeployed, or unexpanded state, the working region 25 has a folded, undeployed, or unexpanded outer cross sectional area perpendicular to the first longitudinal axis 22, respectively. When the balloon 20 is in an expanded or deployed state, the working region 25 has an expanded or deployed cross sectional area perpendicular to the first longitudinal axis 22 that is greater than the folded/undeployed cross sectional area of the balloon 20.

Figures 7B, 7C:
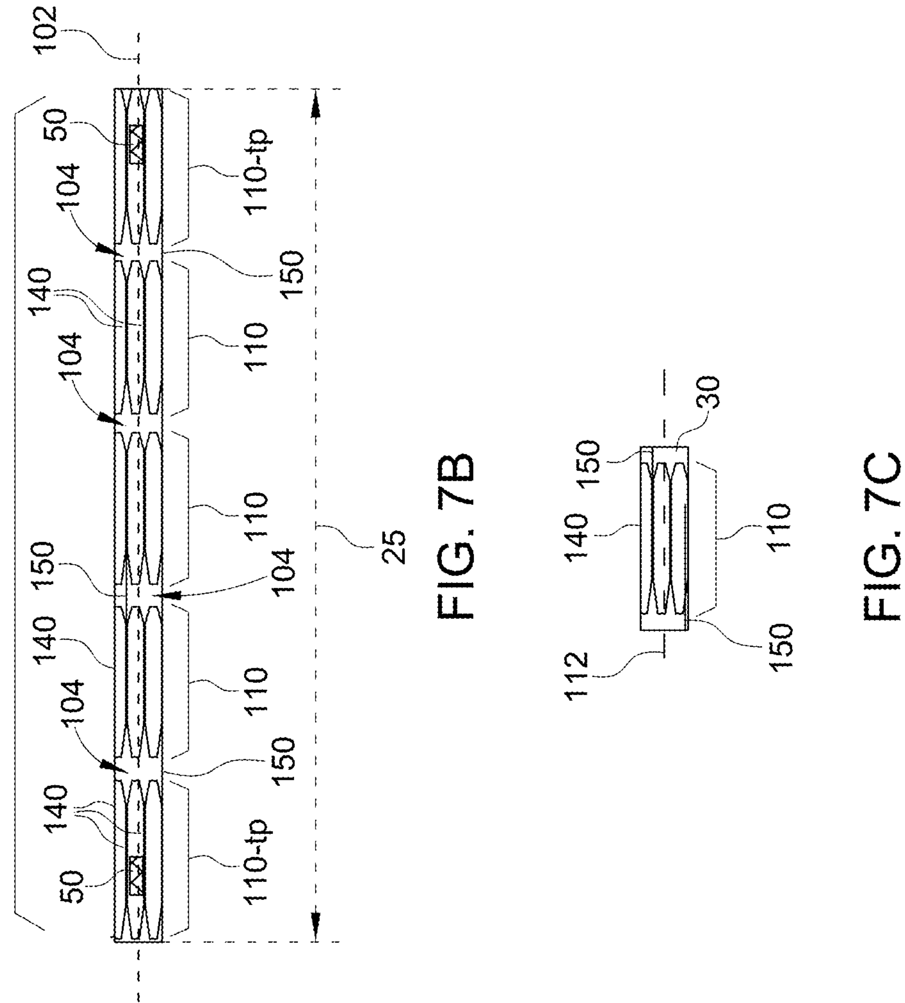
FIG. 7B is a side view showing a tubular spring structure mounted on a working region of a balloon of a scoring balloon catheter in accordance with an embodiment of the present disclosure.
FIG. 7C is a side view showing an annular ring structure of a tubular spring structure mounted on a working region of a scoring balloon catheter's balloon in accordance with an embodiment of the present disclosure.

FIG. 7A additionally shows an elongate tubular spring structure 100 in accordance with an embodiment of the present disclosure, mounted on the folded balloon 20; and FIG. 7B is a side view showing the tubular spring structure 100 mounted on the working region 25 of the folded balloon 20. As indicated in FIG. 7B, the tubular spring structure 100 has a second longitudinal or lengthwise axis 102, which extends along or through a lumen of the tubular spring structure 100 in a manner that individuals having ordinary skill in the relevant art will readily comprehend. When the tubular spring structure 100 is mounted on the balloon 20 and the tubular spring structure 100 and the balloon 20 are in a straight configuration, the first longitudinal axis 22 and the second longitudinal axis 102 are substantially or essentially parallel to each other, or coincident along the balloon's working region 25, as individuals having ordinary skill in the relevant art will also readily comprehend.

In an unexpanded or non-expanded resting state, the tubular spring structure 100 has a resting cross sectional area perpendicular to the second longitudinal axis 102, which is smaller than the folded/undeployed cross sectional area of the balloon's working region 25. The tubular spring structure 100 can be slightly expanded from its resting state and mounted on the working region 25 of the folded balloon 20, in a manner readily understood by individuals having ordinary skill in the relevant art.

As indicated in FIGS. 7A and 7B, the tubular spring structure 100 includes a plurality of annular ring structures 110 that surround portions of the balloon 20 along the working region 25 thereof, and which are physically separated or segregated from each other along the working region 25 of the balloon 20 by spatial gaps 104.

FIG. 7C is a side view showing a particular annular ring structure 110 of the tubular spring structure 110 of FIGS. 7A and 7B. Along its length, each annular ring structure 110 provides a lumen having a central axis 112 lengthwise or longitudinally extending therethrough, and a relaxed cross sectional area perpendicular to its central axis 112, which in the absence of the balloon 20 is less than the folded or undeployed outer cross sectional area of the balloon's working region 25. Each annular ring structure 110 is configured for circumferentially residing around and engaging with a portion or segment of the balloon's working region 25; and each annular ring structure 110 is configured for resilient radial expansion in response to radial forces exerted on the annular ring structure 110 by the balloon 20. When the tubular spring structure 100 is mounted on the balloon 20 and the tubular spring structure 100 and the balloon 20 are in 1*s* a straight configuration, the central axis 112, the second longitudinal axis 102, and the first longitudinal axis 102 are substantially or essentially parallel to each other, or coincident along the balloon's working region 25, as individuals having ordinary skill in the relevant art will readily comprehend.

Figure 8A:
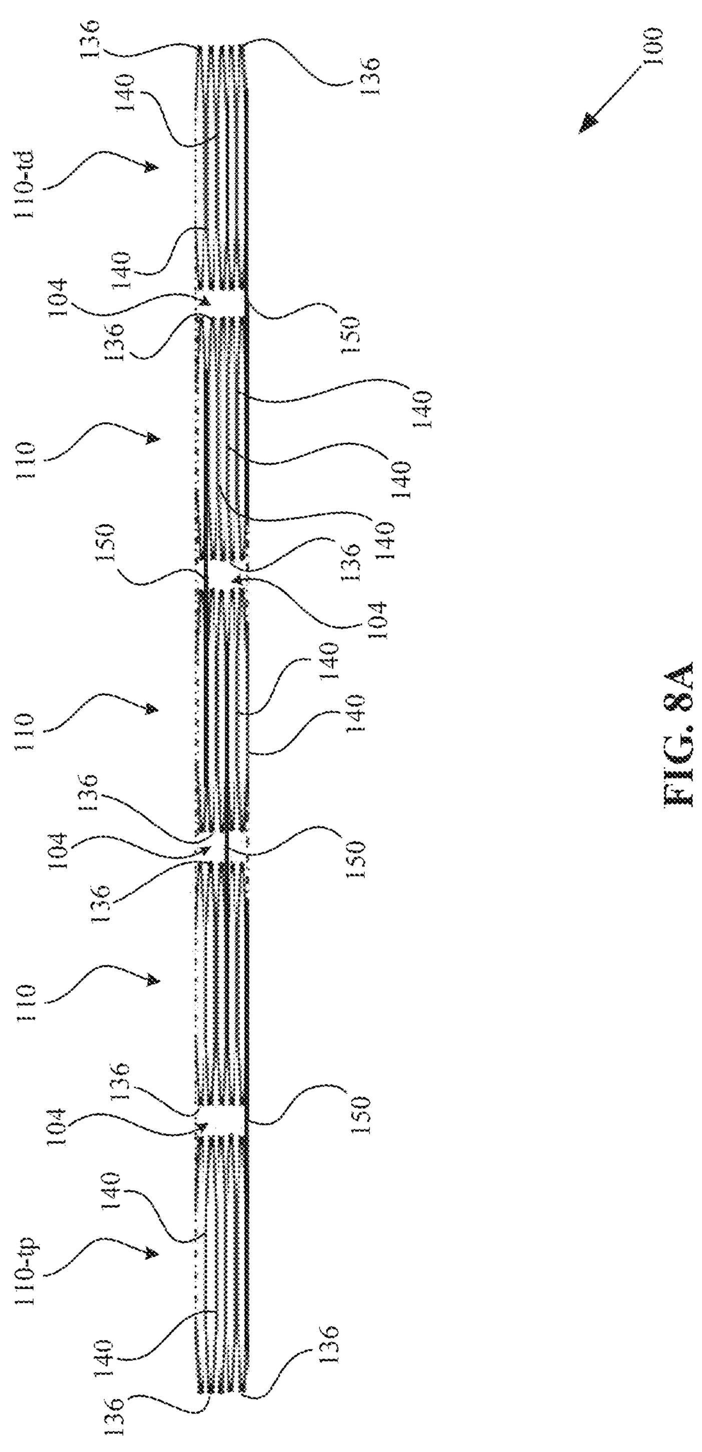
FIG. 8A is a side view showing aspects of a tubular spring structure in accordance with an embodiment of the present disclosure, in a slightly expanded state, cut longitudinally and laid flat.
Figure 8B:
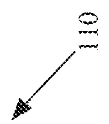
FIG. 8B is a side view showing aspects of an annular ring structure corresponding to FIG. 8A in accordance with an embodiment of the present disclosure, in a slightly expanded state, cut longitudinally and laid flat.
Figure 8B:
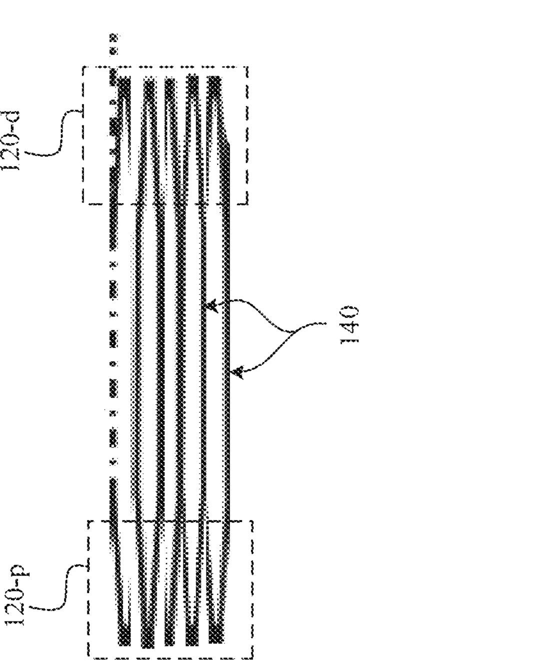
Figure 9A:
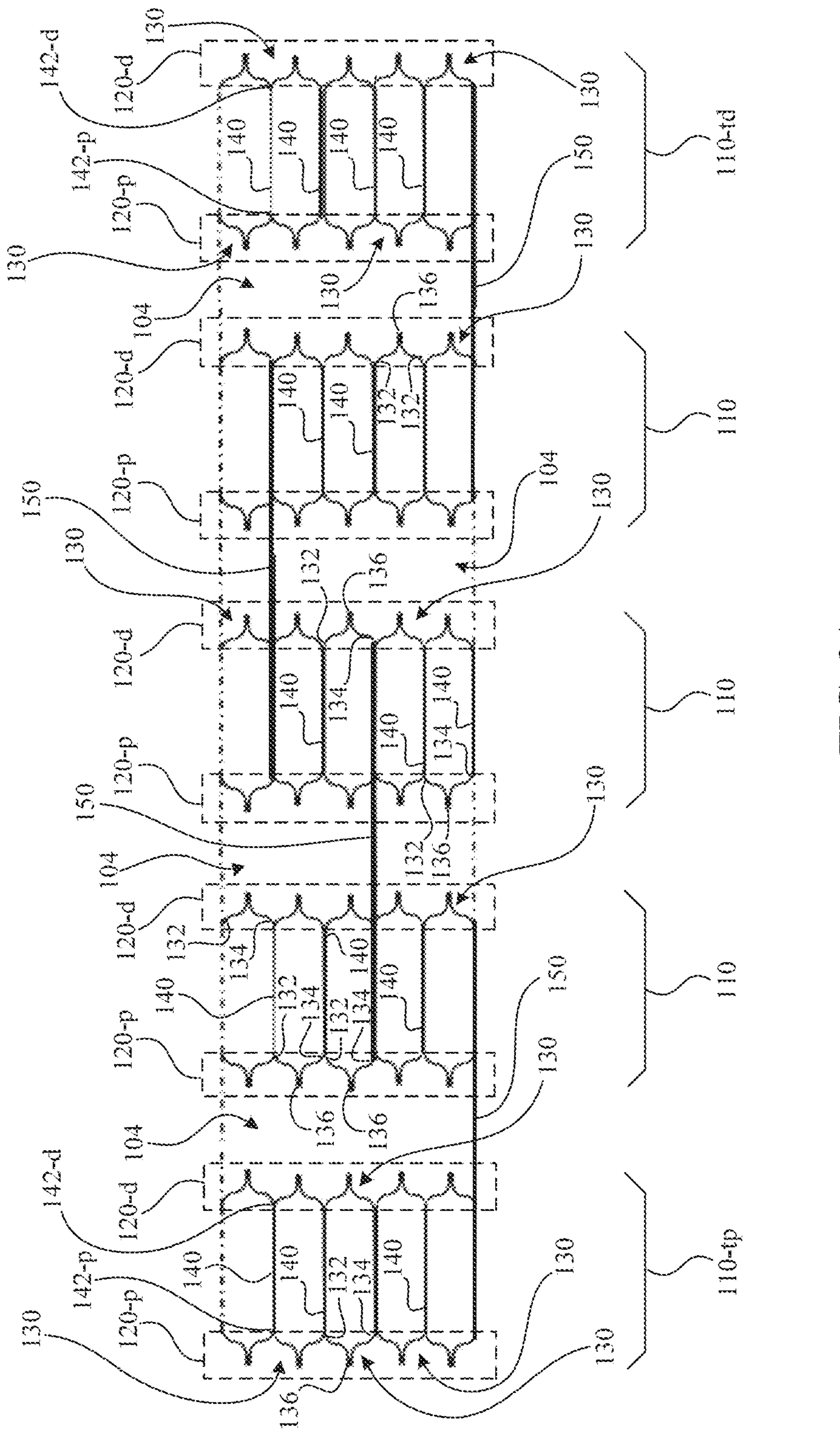
FIG. 9A is a side view showing detailed aspects of an annular ring structure in accordance with an embodiment of the present disclosure, in a fully expanded state, cut longitudinally and laid flat.
Figure 9B:
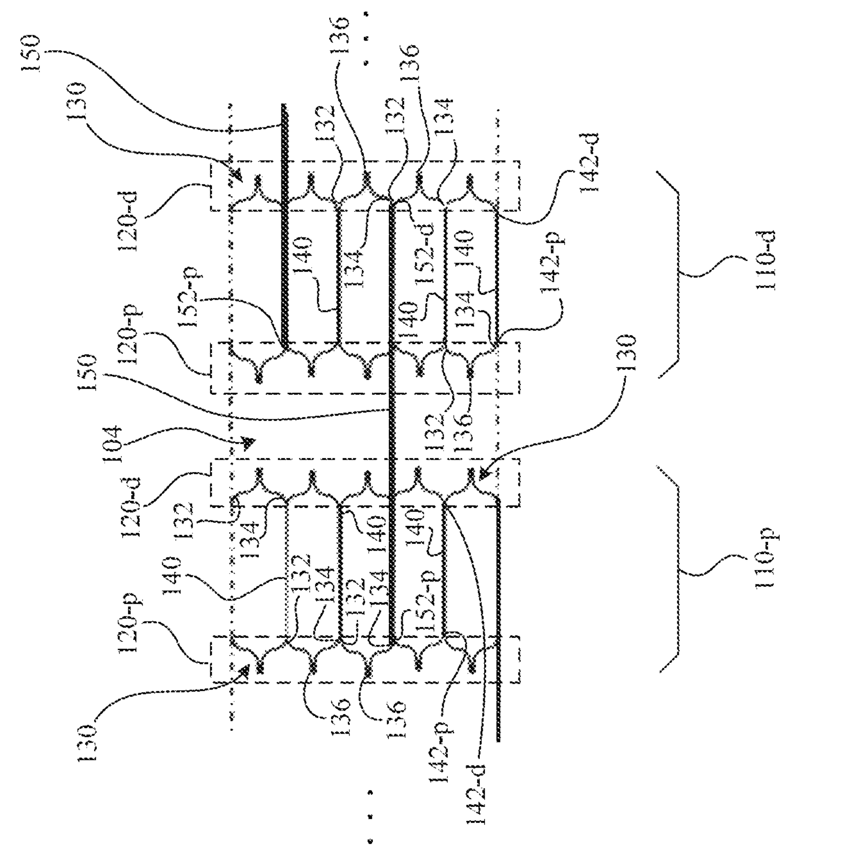
FIG. 9B is a side view of a given or selected pair of serially or directly successive or adjacent annular ring structures of FIG. 9A having a spatial gap therebetween, which can defined as a first or distal annular ring structure and a second or proximal annular ring structure separated by the spatial gap.

FIG. 8A is a side view showing aspects of a tubular spring structure 100 in accordance with an embodiment of the present disclosure, in a slightly expanded state, cut longitudinally and laid flat. FIG. 8B is a side view showing aspects of an annular ring structure 110 of the tubular spring structure 100 corresponding to FIG. 8A in accordance with an embodiment of the present disclosure, in a slightly expanded state, cut longitudinally and laid flat. FIG. 9A is a side view showing more detailed or detailed aspects of an annular ring structure 110 in accordance with an embodiment of the present disclosure, in a fully expanded state, cut longitudinally and laid flat. FIG. 9B is a side view of a given or selected pair of serially or directly successive or adjacent annular ring structures 110 of FIG. 9A, having a spatial gap 104 therebetween, which can defined as a first or distal annular ring structure 110*d* and a second or proximal annular ring structure 110*d* separated by the spatial gap 104.

Further to the foregoing and with reference to FIGS. 7A-12B, the tubular spring structure 100 includes a series of annular ring, band, or sleeve structures or assemblies 110 along its length, which are disposable or disposed along the balloon's working region 25. The tubular spring structure 100 is formed to provide a spatial interval between each annular ring structure 110, e.g., a spatial gap 104 between serially successive consecutive annular ring structures 110 along the length of the tubular spring structure 100. Thus, along a distal to proximal direction (or equivalently, along a proximal to distal direction), spatial gaps 104 exist between each annular ring structure 110. More particularly, serially or directly successive or pairwise adjacent annular ring structures 110 are separated by spatial gaps 104 along the tubular spring structure's length, or analogously, along the balloon's working region 25 when the tubular spring structure 100 is carried by or mounted to the balloon 20. Each annular ring structure 110 has a predetermined length, e.g., an unexpanded length, and is typically elongate; in various embodiments, each annular ring structure 110 has an identical length, e.g., an identical unexpanded length. Notwithstanding, in some embodiments, one or more annular ring structures 110 can have different lengths relative to other annular ring structures 100.

The annular ring structures 110 are coupled or connected by elongate scoring links 150, each of which has a predetermined length. Depending upon the size of a vessel under consideration, in various embodiments the scoring links 150 are between 1.5 mm to 15 mm in length. Moreover, to maximize flexibility and deliverability of the tubular spring structure or the balloon catheter on which it resides into the target lesion site, each scoring link 150 does not span or transverse the entire working region 25 of the balloon 20 (nor the entire length of the tubular spring structure 100). A typical working region 25 of the balloon 20 is in the range of 10 mm-400 mm.

Rather, for each distinct or distinguishable pair of serially or directly successive or adjacent annular ring structures 110, a single scoring link 150, couples or connects the serially or directly successive or pairwise adjacent annular ring structures 110, including across the spatial gap 104 between these serially or directly successive or pairwise adjacent annular ring structures 110. Hence, because of the presence of the spatial gap 104 between serially or directly successive or pairwise adjacent annular ring structures 110, the length of each scoring link 150 is greater than the length of each annular ring structure 110 within the serially or directly successive or pairwise adjacent annular ring structures 110 coupled thereby, and a portion of the scoring link 150 spans or bridges the spatial gap 104. In several embodiments, a distinct scoring link 150 couples a distinct pair of adjacent annular ring structures 110, and this distinct scoring link 150 does not extend to one or more other annular ring structures 110 outside of the distinct pair of adjacent annular ring structures 110 under consideration. Moreover, as further elaborated upon below with reference to FIGS. 9A, 9B, and 10, in several embodiments each annular ring structure 110 within a distinct pair of adjacent annular ring structures 110 includes a pair of annular springs 120*p,d*, and thus the aforementioned distinct scoring link 150 that couples the distinct pair of adjacent annular ring structures 110 couples a total of four springs 120*p,d*.

In multiple embodiments in which the annular ring structures 110 have an equal length, the spatial gap 104 between serially or directly successive or pairwise adjacent annular ring structures 110 is approximately 5%-30% of the length, e.g., the unexpanded length, of each annular ring structure 110. In several embodiments, the length of each scoring link 150 is approximately between 5%-30%, or in certain embodiments approximately 1.5 mm to 15 mm, greater than the combined lengths, e.g., the combined unexpanded lengths, of the pair annular ring structures 110 coupled or connected thereby.

In addition to the foregoing, serially or directly successive scoring links 150 along the length of the tubular spring structure 100 are disposed at different radial positions relative to each other about the second longitudinal axis 102. Thus, a single distinct scoring link 150 couples or connects a distinct pair of serially or directly successive or adjacent annular ring structures 110; and relative to a plane perpendicular to the second longitudinal axis 102, a given scoring link 150 resides at a distinct angle about the second longitudinal axis 102 with respect to any directly successive scoring link 150 and any directly preceding scoring link 150 along the balloon's working region 25.

Each scoring link 150 is configured as a traumatic element with respect to contact with tissue within a vessel, e.g., an intravascular lesion, in which the balloon's working region 25 is disposed. More particularly, as further detailed below, each scoring link 150 carries or is formed (e.g., integrally formed in at least some embodiments) as a set of scoring structures configured for scoring or forming cuts or grooves in intravascular tissue, e.g., longitudinal cuts or grooves, upon contact therewith and displacement (e.g., at least radial displacement) therein and/or therealong.

Figure 10:
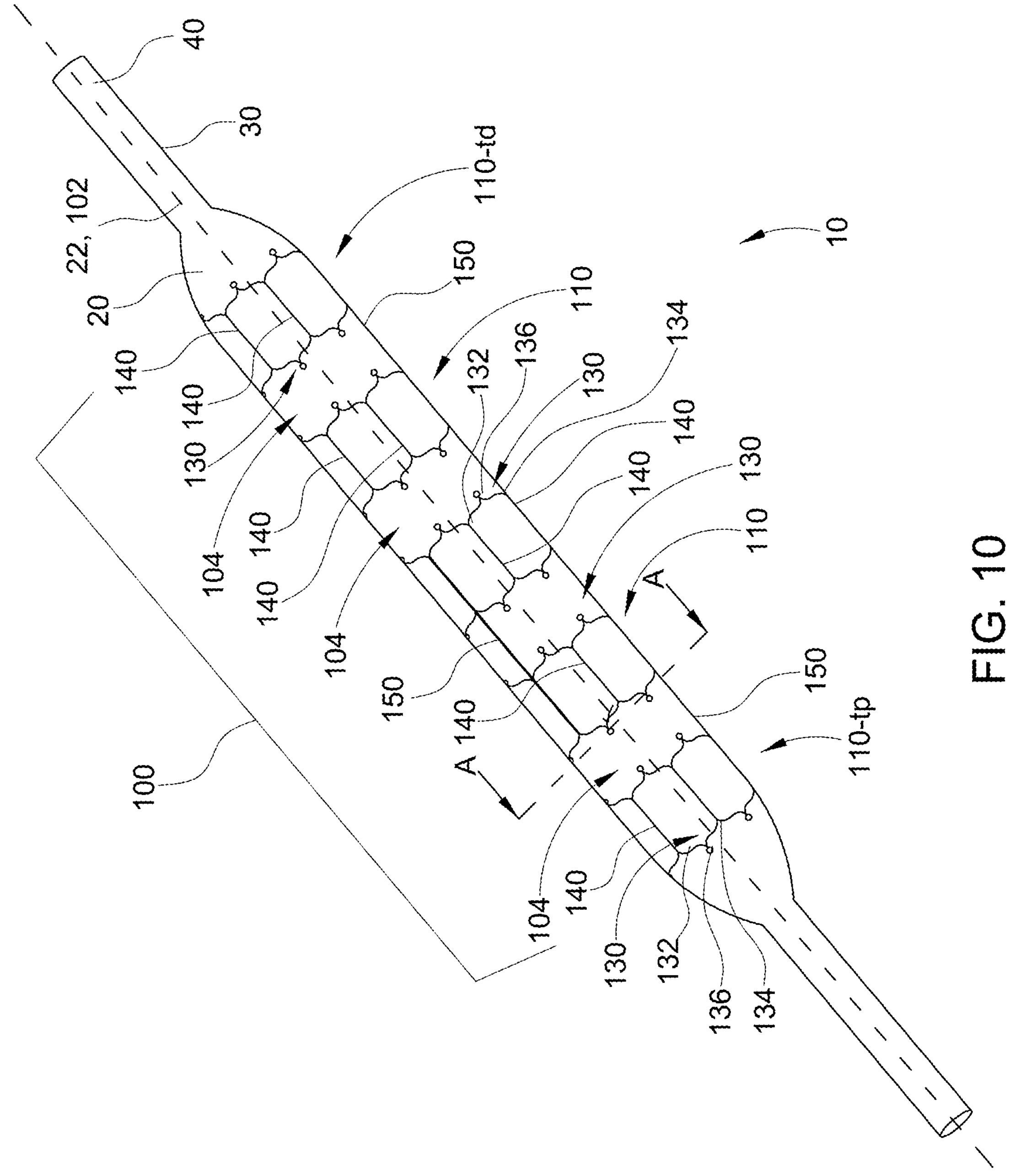
FIG. 10 is a perspective illustration of a scoring catheter in accordance with an embodiment of the present disclosure, illustrating a tubular spring structure in accordance with an embodiment of the present disclosure carried by an angioplasty balloon in a manner suitable for lesion treatment.

With further specific reference to FIGS. 9A, 9B, and 10, in various embodiments each annular ring structure 110 includes or is structured as a distal annular spring 120-*d* and a distinguishable, distinct, or separate proximal annular spring 120-*p*, each of which has a periphery or circumference. e.g., an unexpanded periphery or circumference, and is configured for (a) circumferentially residing around the outer surface of balloon's working region 25; (b) resilient radial expansion relative to a plane perpendicular to the annular ring structure's central axis 112; and (c) exerting an inward circumferential compressive force toward the central axis 112 in response to outward radial expansion away from the central axis 112 beyond the annular ring structure's relaxed cross sectional area.

The distal and proximal annular springs 120-*d*, 120-*p* typically have an identical type of structure, but this need not be the case in all embodiments. In various embodiments, the distal and proximal springs 120-*d*, 120-*p* are each formed of a plurality of spring members 130 that are coupled or connected together to form the periphery or circumference of the distal and proximal springs 120-*d*, 120-*p*, respectively. In multiple embodiments, each spring member 130 includes a pair of terminal ends, e.g., a first end 132 and a second end 134; and an apex or vertex 136 therebetween. A given spring member 130 can include or exhibit a generally or approximately v-shaped or c-shaped profile with respect to or along the periphery or circumference of the spring 120-*d*, 120-*p* of which it is a part. For instance, one or more spring members 130 can include or be in the form of a geometric shape that resembles, approximates, or is essentially identical to a "v" or a "c".

For a given annular ring structure 110, a longitudinal separation distance between its distal and proximal annular springs 120-*d*, 120-*p* corresponding to or establishing a length of the annular ring structure 110 is provided or maintained by a set of spacing elements 140. The set of spacing elements 140 is peripherally disposed around the circumference of the annular ring structure 110 between the distal spring 120-*d* and the proximal spring 120-*p* thereof. In various embodiments, each spacing element 140 extends between the distal and proximal annular springs 120-*d*, 120-*p* with respect to the central axis 112 of the annular ring structure 110, and does not span or bridge the spatial gap 104 between serially or directly successive or pairwise adjacent annular ring structures 110. More particularly, in multiple embodiments each spacing element 140 does not longitudinally extend past or beyond its annular ring structure 110 into the spatial gap 104 between serially or directly successive or pairwise adjacent annular ring structures 110. Hence, in such embodiments, for a given pair of serially or directly successive or adjacent annular ring structures 110, the longitudinal extent of each spacing element 140 (i.e., the spatial extent of the spacing element 140 parallel to the central axis 112 of the annular ring structure 110) is less than 50% of the longitudinal extent of the scoring link 150 (i.e., the spatial extent of the scoring link 150 parallel to the second longitudinal axis 102 of the tubular spring structure 100) that couples or connects these serially or directly successive or pairwise adjacent annular ring structures 110.

In several embodiments, the set of spacing elements 140 includes a plurality of individual spacing elements 140 that are aligned parallel to the central axis 112 of the annular ring structure 110, and which are spaced apart from each other around the circumference of the annular ring structure 110. In such embodiments, each individual spacing element 140 can be a generally straight or essentially straight element having a distal terminal end 142-*d* that couples or connects to the annular ring structure's distal spring 120-*d*, and a proximal terminal end 142-*p* that couples or connects to the annular ring structure's proximal spring 120-*p*. Moreover, for a given individual spacing element 140, its distal terminal end 142-*d* can couple or connect to first and second terminal ends 132, 134 of first and second directly adjacent spring members 130, respectively, of the distal spring 120-*d*, e.g., at a distal junction site; and its proximal terminal end 142-*p* can couple or connect to first and second terminal ends 132, 134 of first and second directly adjacent spring members 130, respectively, of the proximal spring 120-*p*, e.g., at a proximal junction site. For the distal spring 120-*d*, the apex 136 of each spring member 130 can reside between, e.g., midway between, two distal junction sites; and correspondingly, for the proximal spring 120-*p*, the apex 136 of each spring member 130 can reside between, e.g., midway between, two proximal junction sites.

As indicated in FIG. 9B, a given or selected pair of serially or directly successive or adjacent annular ring structures 110 having a spatial gap 104 therebetween can be defined as a first or distal annular ring structure 110-*d* and a second or proximal annular ring structure 110-*p* separated by the spatial gap 104, where (a) the distal annular ring structure 110-*d* has a distal annular spring 120-*d* and a proximal annular spring 120-*p* that are separated by a set of spacing elements 140; (b) the proximal annular ring structure 110-*p* has a distal annular spring 120-*d* and a proximal annular spring 120-*p* that are separated by a set of spacing elements 140; (c) the distal annular spring 120-*d* of the distal annular ring structure 110-*d* forms a distal portion or end of the pair of serially or directly successive or adjacent annular ring structures 110*d*, 110*p*; and (d) the proximal annular spring 120-*p* of the proximal annular ring structure 110-*p* forms a proximal portion or end of the pair of serially or directly successive or adjacent annular ring structures 110*d*, 110*p*. Consequently, the proximal annular spring 120-*p* of the distal annular ring structure 110-*d* resides at a distal side of the spatial gap 104 between the pair of serially or directly successive or adjacent annular ring structures 110-*d*, 110-*p*; and the distal annular spring 120-*d* of the proximal annular ring structure 110-*p* resides at a proximal side of the spatial gap 104 between the pair of serially or directly successive or adjacent annular ring structures 110-*d*, 110-*p*.

In some embodiments, for a given pair of consecutive annular ring structures 110, i.e., a distal annular ring structure 110-*d* serially followed by a proximal annular ring structure 110-*p*, the spatial gap 104 therebetween can be approximated, defined, or measured by a longitudinal length or distance (e.g., an unexpanded longitudinal length or distance) between (a) the proximal terminal end(s) 142-*p* of the spacing elements 140 of the distal annular ring structure 110-*d* or a plane perpendicular thereto at the aforementioned proximal junction site(s) of the distal annular ring structure 110-*d*, and (b) the distal terminal end(s) 142-*d* of the spacing elements 140 of the proximal annular ring structure 110-*p* or a plane perpendicular thereto at the aforementioned distal junction site(s) of the proximal annular ring structure 110-*p*. Additionally or alternatively, the spatial gap 104 can be approximated, defined, or measured by a longitudinal length or distance (e.g., an unexpanded longitudinal length or distance) between (i) a plane across the spring member apices 136 of the proximal spring 120-*p* of the distal annular ring structure 110-*d*, and (ii) a plane across the spring member apices 136 of the distal spring 120-*d* of the proximal annular ring structure 110-*p*.

The scoring links 150 are structurally and functionally distinct from the spacing elements 140, particularly in that the scoring links 150 are structurally configured as traumatic structures and the spacing elements 140 are structurally configured as at least generally atraumatic structures with respect to contact with intravascular tissue. However, the scoring links 150 can couple or connect to distal and proximal springs 120-*d*, 120-*p* of each of the serially or directly successive or pairwise adjacent annular ring structures 110 to which the scoring link 150 corresponds in a manner similar, analogous, or essentially identical to that for the spacing elements 140.

Further in view of the foregoing, in various embodiments the single scoring link 150 that couples or connects the distal annular ring structure 110-*d* and the proximal annular ring structure 110-*p* and which spans or bridges the spatial gap 104 therebetween extends from the distal annular spring 120-*d* of the distal annular ring structure 110-*d* to the proximal annular spring 120-*p* of the proximal annular ring structure 110-*p*. This scoring link 150 is supported along a distal segment or section thereof by the distal annular ring structure 110-*d*, and is supported along a proximal segment or section thereof by the proximal annular ring structure 110-*p*. In several embodiments, the distal and proximal segments of the scoring link 150 that are supported by the distal and proximal annular ring structures 110-*d*, 110-*p* form less than 100% of the scoring link's overall length, e.g., each of the distal and proximal segments of the scoring link 150 that are supported by the distal and proximal annular ring structures 110-*d*, 110-*p* is less than 50% of the scoring link's overall length.

In several embodiments each scoring link 150 has a distal terminal end 152-*d* that couples or connects to first and second terminal ends 132, 134 of first and second directly adjacent spring members 130, respectively, of the distal spring 120-*d* of the distal annular ring structure 110-*d*, e.g., at a corresponding distal junction site; and a proximal terminal end 152-*p* that couples or connects to first and second terminal ends 132, 134 of first and second directly adjacent spring members 130, respectively, of the proximal spring 120-*p* of the proximal annular ring structure 110-*p*, e.g., at a corresponding proximal junction site.

Around the periphery or circumference of a given annular ring structure 110, to maximize flexibility, the annular ring structure's distal and proximal annular springs 130-*d*, 130-*p* are coupled or connected by way of at most two scoring links 150 disposed at a predetermined angular separation from each other in a plane perpendicular to the annular ring structure's central axis 112 (or analogously/equivalently, the second longitudinal axis 102); and this annular ring structure's distal and proximal annular springs 130-*d*, 130-*p* are also coupled or connected by way of the set of spacing elements 140 thereof. It can be noted that for the tubular spring structure 100, a first or distal-most terminal annular ring structure 110-*td* corresponding to the distal portion or end of the tubular spring structure 100 has a single scoring link 150 coupled or connected thereto; and a second or proximal-most terminal annular ring structure 110-*tp* corresponding to the proximal portion of end of the tubular spring structure 100 has a single scoring link 150 coupled or connected thereto. Annular ring structures 110 disposed between the first and second terminal annular ring structures 110-*td*, 110-*tp* have at most two scoring links 150 coupled or connected thereto.

In various embodiments, for a tubular spring structure 100 providing a total of N scoring links 150, the tubular spring structure 100 has a total of (N+1) annular ring structures 110 separated by spatial gaps 104 along its length, which provide N distinct or non-identical pairs of serially or directly successive or adjacent annular ring structures 110 along the length of the tubular spring structure 100. Each distinct or non-identical pair of serially or directly successive or adjacent annular ring structures 110 has a single scoring link 150 spanning or bridging the spatial gap 104 therebetween. Typically, the angular separation between successive scoring links 150 around the second longitudinal axis 102 of the tubular spring structure 100 is given by (360/Y) degrees, where Y is typically (although not necessarily or not always) a number between 3 and 5. In some (though not necessarily all) embodiments, Y equals N. Around the periphery or circumference of a given annular ring structure 110, spacing elements 140 reside at locations other than the position(s) occupied by its scoring link(s) 150. Such spacing elements 140 can be evenly spaced around the periphery or circumference of the annular ring structure relative to each other and the scoring link(s) 150.

With respect to the scoring links 150, each scoring link 150 carries or is formed as a set of scoring structures configured for forming cuts and/or grooves in intravascular tissue(s) in response to contact therewith and displacement in directions along or parallel to the tubular spring structure's second longitudinal axis 102. In response to flexure of the tubular spring structure 100, for example in response to tracking through a curved vessel or lesion, the second longitudinal axis 102 adopts a curvilinear shape. In various embodiments, each scoring link 150 has a geometric shape that is essentially identical to the geometric shape of a segment of the second longitudinal axis 102 to which it most closely resides in response to flexure of the tubular spring structure 100. Thus, prior to flexure of the tubular spring structure 100, e.g., when the tubular spring structure 100 is in an essentially straight configuration (i.e., essentially no curvature exists along the second longitudinal axis 102), each scoring link 150 is an essentially straight longitudinal structure. Thus, each scoring link 150 in such embodiments is configured for making longitudinal cuts or grooves along or parallel to a vessel's central axis. Notwithstanding the foregoing, in certain embodiments, one or more scoring links 150 can include or be curved structures, e.g., corresponding to portions of a spiral or helix, when the tubular spring structure 100 is in an essentially straight or straight configuration, such that at least some scoring links 150 can make curved, e.g., spiral or helical form, cuts or grooves with respect to the vessel's central axis.

Figure 11A:
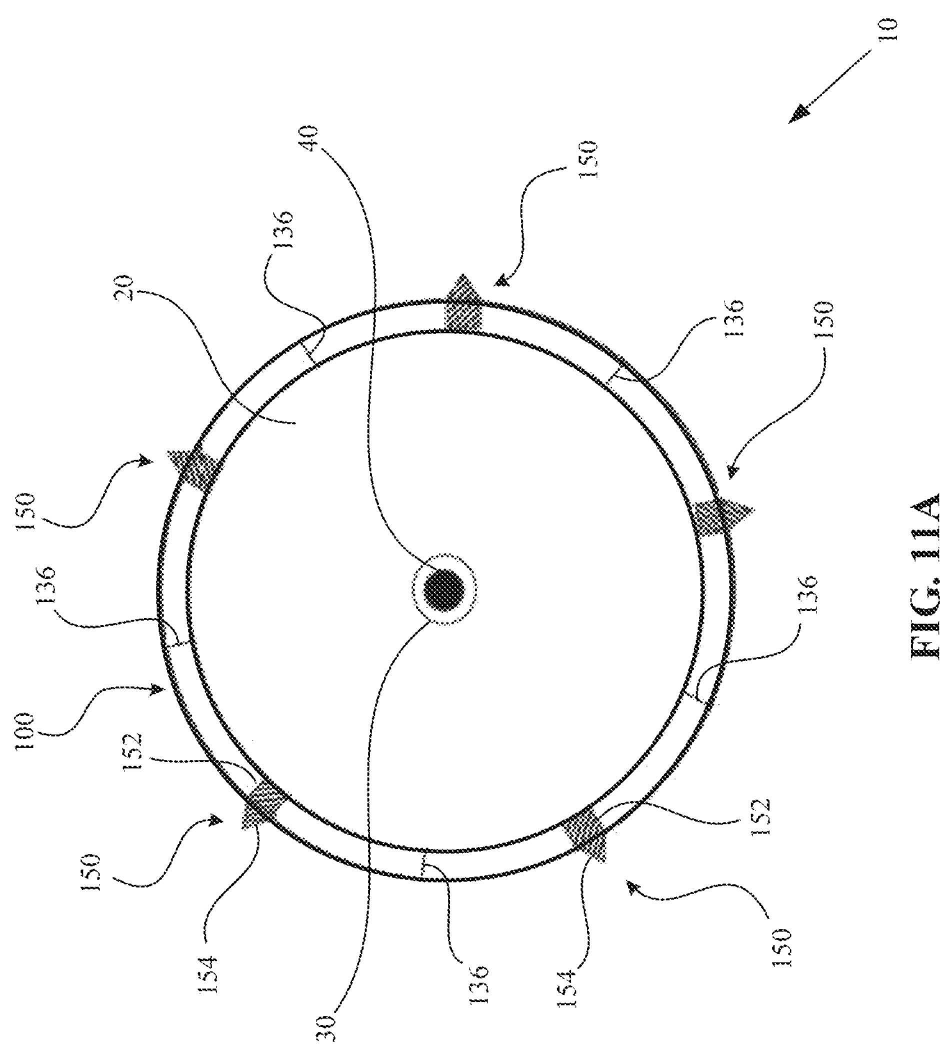
FIGS. 11A-11C are perpendicular cross-sectional illustrations showing a scoring balloon catheter providing a tubular spring structure in accordance with an embodiment of the present disclosure, and further showing representative types of scoring links in accordance with particular embodiments of the present disclosure.
Figure 11B:
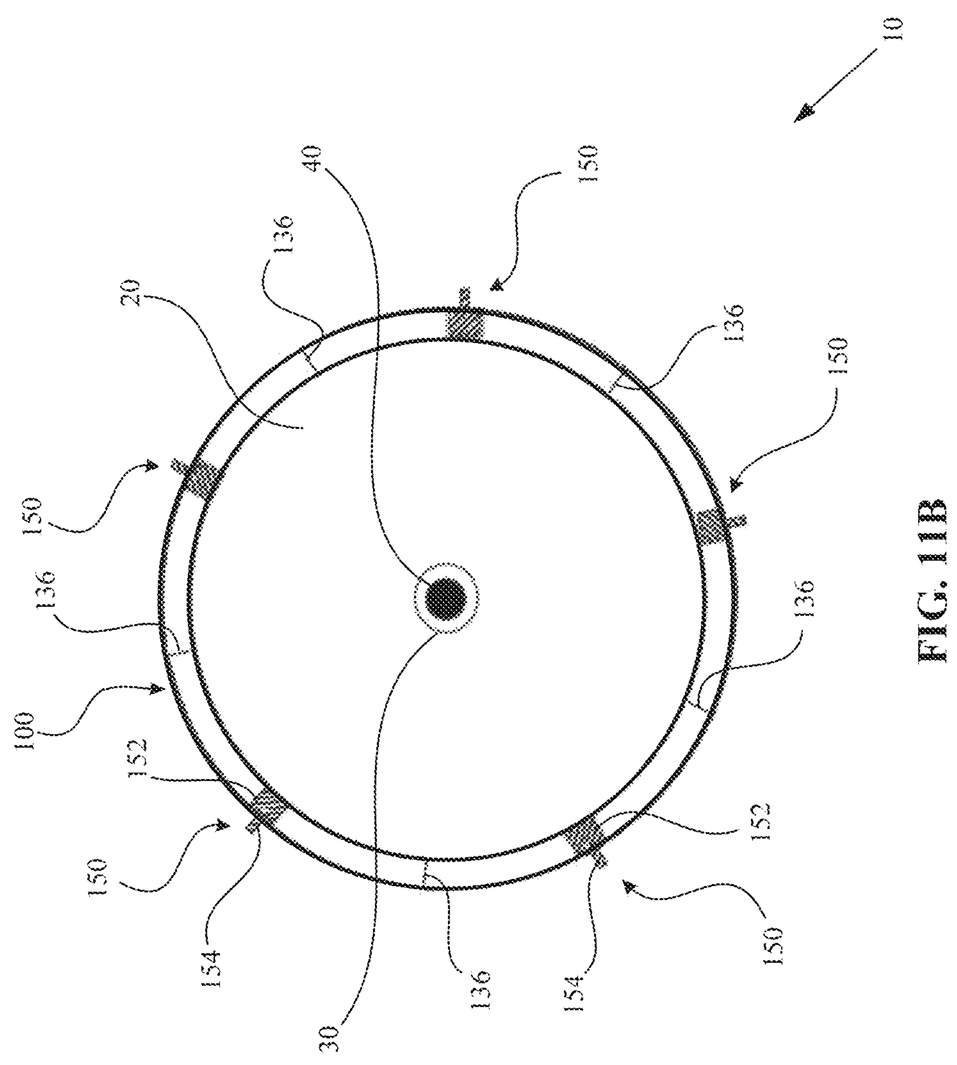
Figure 11C:
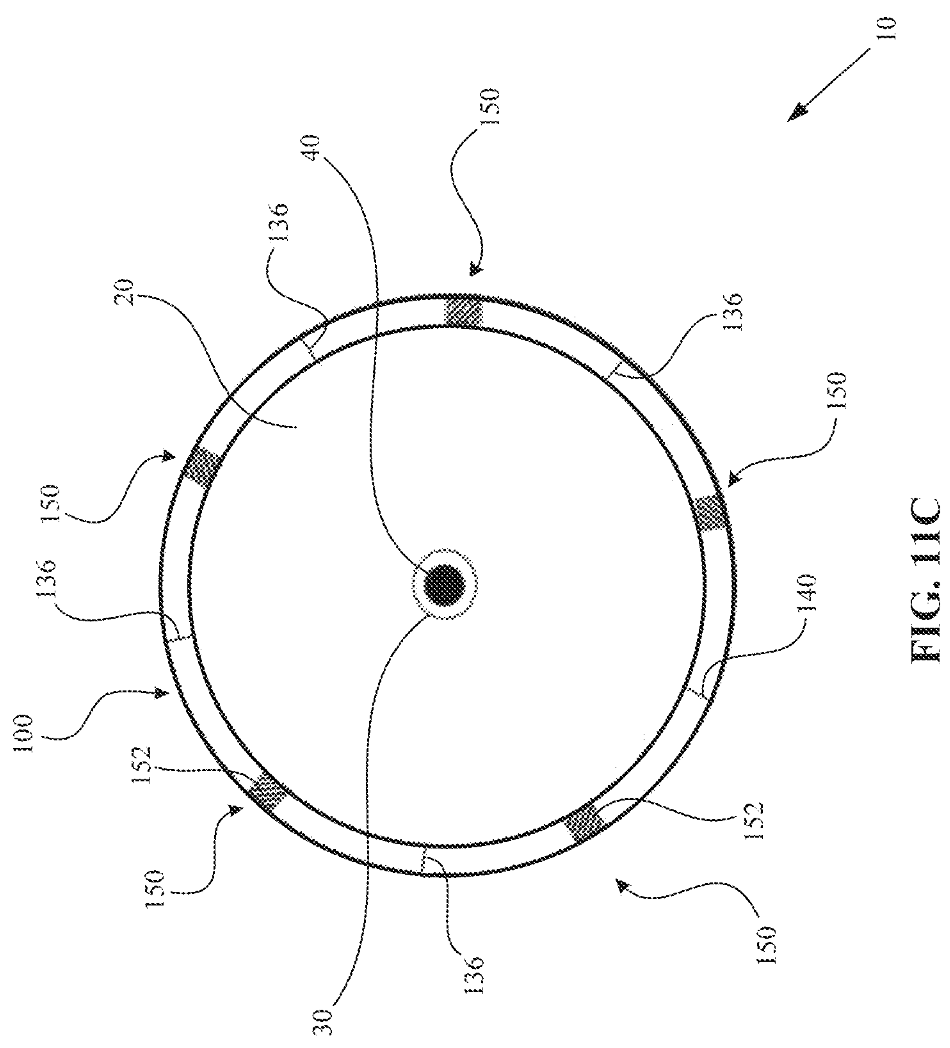

Scoring links 150 or scoring structures carried thereby can exhibit different types of geometric profiles or shapes perpendicular to the second longitudinal axis 112. For instance, FIGS. 11A-11C are representative cross sectional views along a line corresponding to or such as line A-A of FIG. 10, showing portions of a scoring balloon catheter 10 in accordance with particular embodiments of the present disclosure, including an expanded balloon 20 having a representative tubular spring structure 100 mounted thereon, which depending upon embodiment details includes scoring links 150 exhibiting different types of perpendicular cross sectional geometric profiles or shapes. Each of FIGS. 11A-11C show the expanded balloon 20, the balloon tip 30, and the guidewire 40; plus five scoring links 150 and five spacing elements 140 circumferentially disposed about the periphery of the tubular spring structure 110.

In the embodiment shown in FIG. 11A, the scoring links 150 have a trapezoidal perpendicular cross sectional profile or shape, which includes or is defined by a rectangular (e.g., square) base portion 152 having a scoring structure 154 configured as an outwardly projecting triangular segment or spike extending therefrom. Such a triangular portion 154 of each such scoring link 150 can be provided, intended, or utilized for enhanced or deep(er) cutting of a lesion. In various embodiments, the base portion 152 and the triangular portion 154 are formed as an integral structure.

In the embodiment shown in FIG. 11B, each scoring link 150 has a rectangular (e.g., square) perpendicular cross sectional profile or shape, which includes or is defined by a rectangular base portion 152 having a scoring structure 154 configured as a narrow(er) outwardly projecting rectangular or square stub extending therefrom. Such a stub 154 can provide narrow(er), less traumatic cuts or grooves in a lesion. In various embodiments, the base portion 152 and the stub 154 are formed as an integral structure.

In the embodiment shown in FIG. 11C, each scoring link 150 has a rectangular (e.g., square) perpendicular cross sectional profile or shape, which is defined by a base portion 152 that excludes outwardly projecting structures. While the scoring link 150 of FIG. 11C does not carry any shaped elements that outwardly project away from the base portion 152, this type of scoring link 150 is still useful or effective with respect to forming cuts or grooves in a lesion, and hence such scoring link 150 itself can be defined as a type of scoring structure. Scoring links 150 of the type shown in FIG. 12 are typically easiest to manufacture, and can thus reduce manufacturing cost.

The scoring links 150, a set of scoring structures 154, and/or one or more other portions of the tubular spring structure 100 can be coated with at least one therapeutic substance. A therapeutic substance may be a pharmaceutically active agent, for example a potent antiproliferative agent for human smooth muscle cells, or a chemoactive agent suitable for cancer treatment. The antiproliferative agent may be a microtubule inhibitor such as paclitaxel, or prodrugs thereof, or mTOR inhibitors from the 'LIMUS' class of drugs which have found wide application in coating Drug Eluting Stents. Suitable coating antiproliferative drug coating formulations and coating methods may be found in U.S. Pat. Nos. 7,682,387, 9,974,931, 9,757,544, 9,220,875, EP3228335A1, EP1372737A2, U.S. Pat. No. 9,492,594B2, U.S. Pat. No. 8,414,910B2, WO2004028582A1, and DE202008018649U1 which are incorporated herein by reference in their entirety.

With respect to their perpendicular cross sections, the spacing elements 140 can be narrower or wider than the base portions 152 of the scoring links 150, depending upon embodiment details. A spacing element or each spacing element 140 can have, for instance, a perpendicular cross sectional width that is between 50% to 500% of the perpendicular cross sectional width of the base portion 152 of a scoring link or each scoring link 150. Spacing elements 140 can be formed such that outwardly facing portions thereof are as smooth or atraumatic as possible; for instance, spacing elements 140 can be formed as rounded or round structures (e.g., rounded/chamfered flat rectangular or round wire elements) in order to reduce or minimize the extent to which they are traumatic with respect to contact with intravascular tissue.

A tubular spring structure 100 configured in accordance with an embodiment of the present disclosure, such as described above, or a scoring balloon catheter 10 having such a tubular spring structure 100, exhibits high or very high flexibility in essentially all bending planes away from the second longitudinal axis 112 (e.g., essentially all bending planes away from a plane perpendicular to the second longitudinal axis 112), and thus is very well-suited for deployment and use in highly tortuous vascular passages. Moreover, a tubular spring structure 100 in accordance with an embodiment of the present disclosure exhibits good, very good, or excellent scoring capability, e.g., highly effective intravascular tissue cutting capability. Such high or very high flexibility concurrent with excellent tissue scoring capability directly arises from the structural configuration of the tubular spring structure 100, in that:

(a) excellent flexibility exists because (i) each annular ring structure 110 is formed of a pair of radially flexible or expandable springs 120-*d*, 120-*p*; (ii) within the expected or normal limits of balloon expansion, e.g., for the treatment of cardiovascular lesions, each annular ring structure 110 and each scoring link 150 is configured for elastic expansion and deformation, while remaining below or well below its plastic deformation limit; (iii) serially or directly successive or pairwise adjacent annular ring structures 110 are separated by spatial gaps 104 along the tubular spring structure's length, which provides for easy articulation of successive annular ring structures 110 and aids dimensional stability of the annular ring structures 110; (iv) only a single scoring link 150 couples or connects each annular ring structure 110 of a given distinct or non-identical pair of serially or directly successive or adjacent annular ring structures 110, which provides the tubular spring structure 100 with enhanced flexibility; and (v) the dimensions, including lengths, of the annular ring structures 110, including their distal and proximal springs 120-*d*, 120-*p* and spacing elements 140, relative to the dimensions, including lengths, of the scoring links 150 and the spatial gaps 104 facilitates or enhances flexibility; and (b) enhanced or excellent scoring capability exists because (i) the length of each scoring link 150 relative to the lengths of its corresponding pair of annular ring structures 110 and the spatial gap 104 bridged thereby means that the scoring link 150 is structurally supported across significant portions of its length corresponding to a distal section and a proximal section of the scoring link 150 that are carried by a distal and a proximal annular ring structure 110-*d*, 110-*p*, respectively, which means that outward radial forces exerted by the balloon 20 upon the scoring link 150 are enhanced and can be effectively or more effectively directed, concentrated, or applied to intravascular tissue as tissue cutting or separation forces.

In various embodiments, the tubular spring structure 100 typically includes or is in the form of a metal mesh structure, e.g., having circumferentially or radially expandable metal annular ring structures 110. The spacing elements 140 and the scoring links 150 can include or be made of wire, where the spacing elements 140 are structured as at least generally atraumatic elements, and the scoring links 150 are structured as traumatic elements with respect to (intra)vascular tissue (s).

Such a metal mesh structure is typically between 100-1000 microns thick (e.g., approximately 250 microns). The thickness of the structure may be determined by the depth of the grooves or cuts intended or needed in a particular type of lesion under consideration, and the intended or needed flexibility of the tubular spring structure 100/scoring catheter 10 for ease of delivery to tortuous vascular pathways and/or lesions therealong or therein. A mesh structure of lower thickness will make the balloon portion 20 of the scoring catheter 10 more flexible. The length of the tubular spring structure 100 can be determined by expected or actual characteristics of the lesion, and may typically be in the range of 20 mm to 250 mm for vascular lesions, with a typical maximum diameter of up to 15 mm.

The metal mesh structure is typically laser cut from steel minitube. However, other methods of forming or manufacturing the metal mesh structure are possible, including cutting and rolling from a flat sheet, electrodeposition, printing, electrical discharge machining, and masking and chemical etching. The metal mesh structure is typically made from high carbon steel, for example SAE1070-1090; however, other metals or metal alloys can be used so long as they satisfy the requirements of maintaining adequate constrictive force when slightly expanded to firmly grip the folded balloon 20, and adequate expansion range while incurring minimal, negligible, or essentially no plastic deformation while accommodating the expanded size of the angioplasty balloon needed to treat and expand the intended lesion.

In general, scoring links 150 having a given perpendicular cross sectional geometric profile or shape may be manufactured by z-axis laser machining of the aforementioned steel minitube.

However, other processes to obtain an intended or desired geometric profile or shape are feasible, including masking and chemical etching.

In at least some embodiments, retention of the tubular spring structure 100 on the catheter 10 is provided by a tubular collar 180 and at least one tether 182, e.g., a single tether 182 or a pair of wire tethers 182, which is/are optionally provided and is/are mounted to the shaft of the catheter 10 proximal to the folded balloon 20. The wire tether(s) 182 can be coupled or attached to the tubular spring structure 100 when desired or required to prevent slippage of the tubular spring structure 100 during expansion of the balloon 20.

Depending upon embodiment details, the tubular spring structure 100 can be secured to the scoring balloon catheter 10 in another or an additional manner. As indicated above, in its unexpanded state, the tubular spring structure 100 has a cross-sectional area or diameter perpendicular to the second longitudinal axis 112 that is slightly smaller than the outer diameter of the section of the folded angioplasty balloon 20 located at the distal end or tip of the scoring balloon catheter 10 to which the tubular spring structure 100 has been mounted. Thus, the tubular spring structure 100 resists dislodgment from the balloon 20 during insertion and tracking into a blood vessel or other vascular conduit as it travels enroute to a target site, area, or region to be treated inside the vessel.

However, in some applications it may be desirable to provide stronger securement of the tubular spring structure to portions of the scoring balloon catheter 10, for instance, if the catheter 10 is being inserted into a particularly narrow or tortuous lesion in the vessel; or alternatively, after scoring treatment if the balloon 20 does not rewrap and deflate precisely, which can cause a risk of downstream embolization of the tubular spring structure 100 in spite of the contractive efforts of the tubular spring structure 100 to remain co-located with the angioplasty balloon 20.

Figures 12A, 12B:
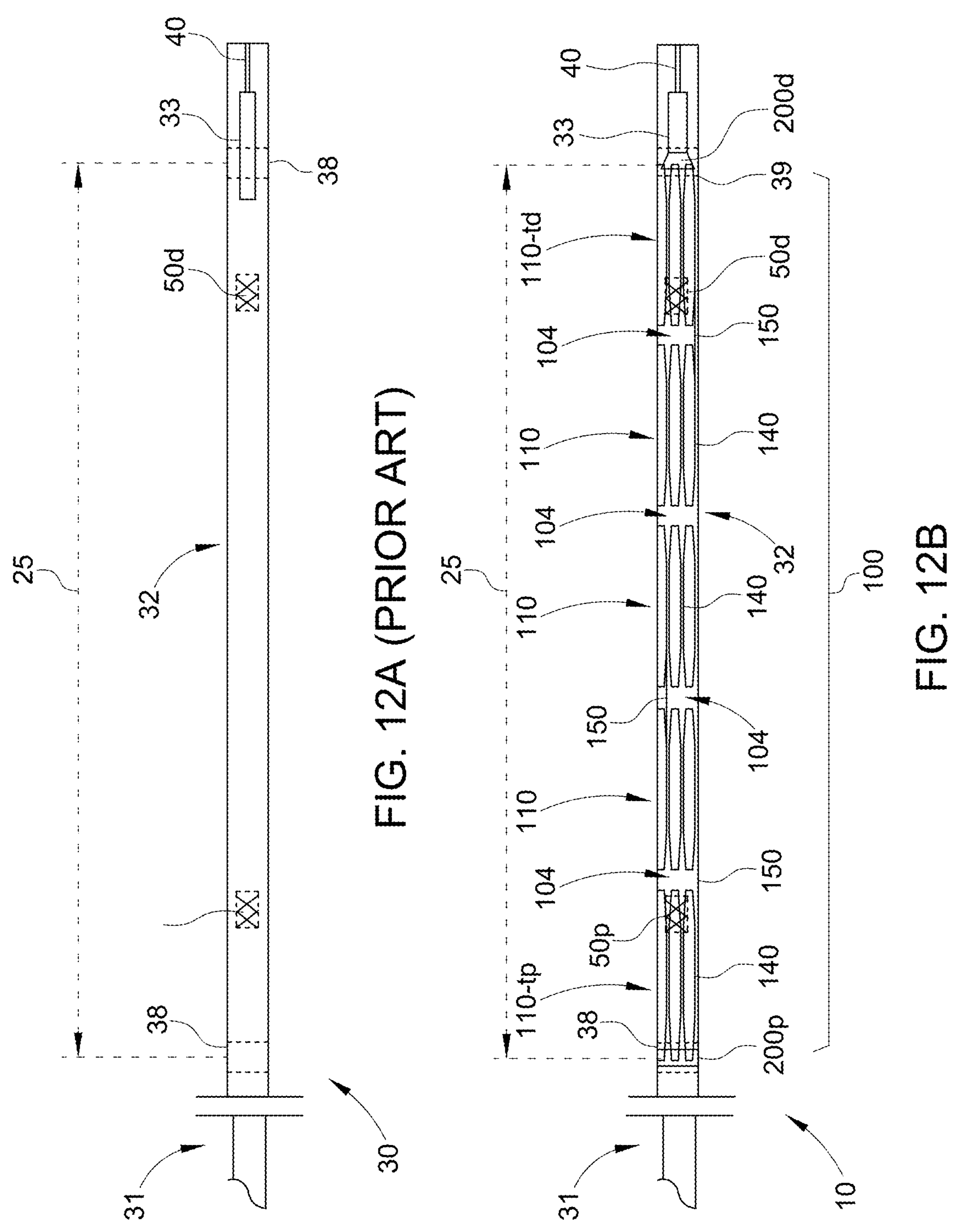
FIGS. 12A and 12B are device side views respectively illustrating a conventional angioplasty balloon catheter structure and an angioplasty balloon catheter-tubular spring structure in accordance with certain embodiments of the present disclosure, showing another manner of providing retention or securement of the tubular spring structure to particular portions of an angioplasty balloon catheter in accordance with certain embodiments of the present disclosure.

FIGS. 12A and 12B illustrate aspects of another or an additional manner of providing retention or securement of the tubular spring structure 100 to particular or predetermined portions of the angioplasty balloon catheter 10 in accordance with certain embodiments of the present disclosure. More particularly, FIG. 12A shows an angioplasty balloon 20 located on a distal portion of an angioplasty balloon catheter 30 to which the tubular spring structure 100 is to be mounted. As indicated in FIG. 12A, the catheter 30 includes a proximal shaft portion or proximal shaft 31, which contains a guidewire lumen through which a guidewire 40 can extend, and a balloon inflation lumen in a manner well known to individuals having ordinary skill in the relevant art. The catheter 30 also includes a distal shaft portion or distal shaft 32 that carries the angioplasty balloon 20. The catheter's distal shaft 32 also carries proximal and distal radiopaque markers 50*p,d* that indicate or define the working length of the balloon 20, such that when the balloon is expanded, balloon shoulders are located approximately circumferentially over these markers 50*p,d* in a manner also readily understood by individuals having ordinary skill in the relevant art. Such individuals will further understand that (a) the working length 25 of the balloon 20 corresponds to or defines a region, area, or spatial extent of the balloon 20 over which outward force can be applied to the vessel lumen upon or in response to expansion of the balloon 20; (b) the distal shaft 32 includes a distal tip 33; and (c) the catheter's distal shaft 32 includes proximal and distal sections, segments, or zones 38, 39 at which the unexpandable proximal and distal ends, respectively, of the parison of the balloon 20 are bonded to the catheter's distal shaft 32.

FIG. 12B illustrates a flexible scoring balloon catheter structure 10 providing a tubular spring structure 100 in accordance with an embodiment of the present disclosure. As part of forming or assembling the flexible scoring balloon catheter structure 10, the tubular spring structure 100 can be positioned and mounted relative to or over the balloon 20 of the catheter 30 such that proximal and distal portions or ends of the tubular spring structure 100 are respectively aligned with the catheter's proximal and distal zones 38, 39 around the circumference of the catheter's distal shaft 32. One or more types of adhesive materials or adhesives can then be applied to the proximal and distal portions or ends of the tubular spring structure 100 that are respectively aligned with the proximal and distal catheter zones 38, 39, about at least portions of the circumference of the distal shaft 32 at which such zones 38, 39 reside, to respectively mechanically or adhesively bond the proximal and distal portions or ends of the tubular spring structure 100 to the unexpandable proximal and distal segments of the parison of the balloon 20 and/or portions of the proximal and distal catheter zones 38, 39, respectively, e.g., circumferentially around the corresponding circumference of the distal shaft 32. The tubular spring structure 100 is thus retained or secured in position, and more particularly, proximal and distal portions or ends of the tubular spring structure 100 are adhered, bonded, or secured to the unexpandable proximal and distal segments of the parison of the balloon 20 and/or portions of the proximal and distal catheter zones 38, 39, by way of proximal and distal adhesive bonds 200*p,d*, respectively. Adhesive materials such as methacrylate and/or thermal plastic adhesives can be used to create such bonds 200*p,d*.

In some embodiments, the distal bond 200*d* can be a relatively weaker or weak adhesive bond compared to the proximal bond 200*p* (e.g., the distal bond 200*d* is intentionally formed to be weaker than the proximal bond 200*p*, such as by way of a different adhesive material, less adhesive material, and/or fewer adhesion points), such that the distal bond 200*d* is strong enough to retain the tubular spring structure in an intended configuration or position during catheter delivery into tight lesions, but is easily broken upon pressurized expansion of the balloon 20; whereas the proximal bond 200*p* is sufficiently strong to keep the tubular spring structure 100 firmly secured, adhered, or attached to the catheter's distal shaft 32 during the treatment procedure as well as subsequent catheter removal from the vessel or vascular structure.

While specific non-limiting representative embodiments have been described, individuals having ordinary skill in the relevant art will, in view of the description herein, be able to make modifications or variations which remain within the scope of the present disclosure and representative examples above.

The invention claimed is:

1. A flexible elongate tubular spring structure for a flexible scoring balloon catheter configured for insertion into a vessel within a mammalian cardiovascular system or other fluid or air carrying conduit or duct within a living mammalian body, the scoring balloon catheter comprising an inflatable elongate balloon having a working region spanning a length, an outer surface along its working region, a first internal passage along which a guide wire is insertable, a second internal passage for passage of a pressurized fluid in communication with the interior of the balloon, and a first longitudinal axis centrally aligned with and extending through the first internal passage, wherein the working region of the balloon in a folded, undeployed, or unexpanded state respectively has a folded, undeployed, or unexpanded outer cross sectional area perpendicular to the first longitudinal axis, wherein the working region of the balloon in an expanded or deployed state respectively has an expanded or deployed outer cross sectional area perpendicular to the first longitudinal axis that is greater than the folded outer cross sectional area, the undeployed outer cross sectional area, and the unexpanded cross sectional area, and wherein the tubular spring structure has a distal end, a proximal end, a length therebetween within which a lumen resides, and a second longitudinal axis centrally aligned with its lumen, and wherein the tubular spring structure comprises:

(i) a plurality of annular ring structures, each annular ring structure having an unexpanded length and providing along its length a lumen having a central axis longitudinally extending therethrough and a relaxed cross sectional area perpendicular to the central axis which in the absence of the balloon is less than the folded, undeployed, or unexpanded outer cross sectional area of the balloon's working region, wherein each annular ring structure is configured for circumferential engagement with the outer surface of the balloon such that the central axis of the annular ring structure is longitudinally aligned with a portion of the first longitudinal axis, wherein each annular ring structure is configured for resilient expansion in radial directions perpendicular to the central axis including outward radial expansion away from the central axis in response to radial forces exerted on the annular ring structure by expansion of the balloon, and wherein each annular ring structure of the plurality of annular ring structures comprises each of:

(a) a distal annular spring having a circumference and configured for circumferentially residing around the outer surface of the balloon, wherein the distal annular spring is configured for resilient radial expansion relative to a plane perpendicular to the central axis, and wherein the distal annular spring is configured for exerting an inward circumferential compressive force toward the central axis in response to outward radial expansion of the distal annular spring away from the central axis beyond the relaxed cross sectional area;

(b) a proximal annular spring longitudinally separated from the distal annular spring, the proximal annular spring having a circumference and configured for circumferentially residing around the outer surface of the balloon, wherein the proximal annular spring is configured for resilient radial expansion relative to a plane perpendicular to the central axis, and wherein the proximal annular spring is configured for exerting an inward circumferential compressive force toward the central axis in response to outward radial expansion of the proximal annular spring away from the central axis beyond the relaxed cross sectional area;

and (c) a set of spacing elements peripherally disposed around the annular ring structure, and further disposed between the distal annular spring of the annular ring structure and the proximal annular spring of the annular ring structure, wherein the set of spacing elements couples the distal annular spring of the annular ring structure to the proximal annular spring of the annular ring structure and maintains a longitudinal separation distance between the distal annular spring of the annular ring structure and the proximal spring of the annular ring structure;

wherein each distinct pair of adjacent annular ring structures of the plurality of annular ring structures is longitudinally organized as a first annular ring structure disposed distal to and separated by the longitudinal spatial gap from a second annular ring structure, wherein the proximal annular spring of the first annular ring structure resides at a distal side of a longitudinal spatial gap that separates the first annular ring structure from the second annular ring structure, and wherein the distal annular spring of the second annular ring structure resides at a proximal side of the longitudinal spatial gap that separates the first annular ring structure from the second annular ring structure; and (ii) a plurality of scoring links, wherein each scoring link has a length, wherein for each distinct pair of adjacent annular ring structures within the plurality of annular ring structures only a single scoring link extends from the distal annular spring of the first annular ring structure to the proximal annular spring of the second annular ring structure such that the single scoring link structurally couples the distinct pair of adjacent annular ring structures and spans the longitudinal spatial gap that separates the first annular ring structure from the second annular ring structures of the distinct pair of annular ring structures, wherein each scoring link comprises a set of scoring structures along at least portions of its length, wherein each scoring structure is configured as a traumatic element with respect to contact with tissue within the vessel, conduit, or duct, wherein serially successive scoring links along the length of the tubular spring structure are disposed at or indexed across different radial positions relative to each other about a circumference of the second longitudinal axis, and wherein the length of each scoring link is greater than the unexpanded length of each annular ring structure within the adjacent pair of annular ring structures coupled thereby.

2. The tubular spring structure of claim 1, wherein each of the distal annular spring and the proximal annular spring has a cross sectional area perpendicular to the central axis which in the absence of the balloon is less than the folded, undeployed, or unexpanded outer cross sectional area of the balloon.

3. The tubular spring structure of claim 1, wherein each scoring link has a length greater than 200% of the unexpanded length of a shortest annular ring structure within the pair of adjacent annular ring structures coupled thereby.

4. The tubular spring structure of claim 1, wherein for each distinct pair of adjacent annular ring structures, the longitudinal spatial gap between the annular ring structures thereof is at least 0.3 mm when the balloon is fully expanded, and wherein the length of the single scoring link that couples the distinct pair of adjacent annular ring structures is between 5%-30% greater than a combined length of the distinct pair of annular ring structures coupled thereby.

5. The tubular spring structure of claim 1, wherein for each distinct pair of adjacent annular ring structures, spacing elements of the distinct pair of adjacent annular ring structures do not span or bridge the longitudinal spatial gap between the distinct pair of adjacent annular ring structures, and wherein a longitudinal extent of each spacing element parallel to the central axis of each annular ring structure of each distinct pair of adjacent annular ring structures is less than 50% of the length of the single scoring link coupling the distinct pair of adjacent annular ring structures parallel to the second longitudinal axis of the tubular spring structure.

6. The tubular spring structure of claim 1, wherein each spacing element has a width that is between 50% to 500% of the width of each scoring link and/or a scoring element carried thereby.

7. The tubular spring structure of claim 1, wherein for each annular ring structure the set of spacing elements includes a plurality of distinct spacing elements longitudinally aligned with the central axis, and wherein the tubular spring structure has a total of N scoring links and (N+1) annular ring structures.

8. The tubular spring structure of claim 7, wherein an angular separation between serially successive scoring links around the second longitudinal axis is (360/Y) degrees, where Y is a number between 3 and 5.

9. The tubular spring structure of claim 1, wherein the distal annular spring comprises a plurality of spring members that are coupled together around the circumference of the distal annular spring.

10. The tubular spring structure of claim 1, wherein the proximal annular spring comprises a plurality of spring members that are coupled together around the circumference of the proximal annular spring.

11. The tubular spring structure of claim 9, wherein each spring member includes a first end segment, a second end segment, and an apex therebetween, and wherein each end segment of each spring member is coupled to one of a spacing element and a scoring link.

12. The tubular spring structure of claim 10, wherein each spring member includes a first end segment, a second end segment, and an apex therebetween, and wherein each end segment of each spring member is coupled by a spacing element.

13. The tubular spring structure of claim 1, wherein at least one of:

(a) the distal annular spring comprises a plurality of spring members that are coupled together around the circumference of the distal annular spring and the plurality of spring members of the distal annular spring includes spring members that exhibit a v-shaped or c-shaped profile with respect to or along the periphery or circumference of the distal annular spring; and (b) the proximal annular spring comprises a plurality of spring members that are coupled together around the circumference of the proximal annular spring and the plurality of spring members of the proximal annular spring includes spring members that exhibit a v-shaped or c-shaped profile with respect to or along the periphery or circumference of the proximal annular spring.

14. The tubular spring structure of claim 1, wherein the second longitudinal axis adopts a curvilinear or curved shape in response to flexure of the tubular spring structure, and wherein when the tubular spring structure is in a straight configuration such that no curvature exists along the second longitudinal axis, (a) each scoring link is a straight longitudinal structure, or (b) one or more scoring links include or are curved structures corresponding to portions of a spiral or helix.

15. The tubular spring structure of claim 1, wherein each scoring structure within the set of scoring structures is elongate and is longitudinally aligned with the second longitudinal axis.

16. The tubular spring structure of claim 1, wherein each scoring link has a scoring structure integrally formed thereon, or integrally forms a scoring structure.

17. The tubular spring structure of claim 1, wherein each scoring structure has a rectangular, trapezoidal, or raised blade cross-sectional shape perpendicular to the second longitudinal axis.

18. The tubular spring structure of claim 1, wherein each spacing element within each annular ring structure of a distinct pair of adjacent annular ring structures is elongate and is longitudinally aligned with the central axis, and each spacing element within each annular ring structure of the distinct pair of adjacent annular ring structures has a length that is at least 40% of the length of the single scoring link that couples the distinct pair of adjacent annular ring structures.

19. The tubular spring structure of claim 1, wherein each annular ring structure comprises a metal mesh.

20. The tubular spring structure of claim 1, wherein the tubular spring structure is formed of at least one metal or metal alloy.

21. The tubular spring structure of claim 1, wherein the tubular spring structure is integrally formed from a metal tube.

22. The tubular spring structure of claim 1, wherein at least portions of at least some of the plurality of scoring links of the tubular spring structure and/or one or more other portions of the tubular spring structure carry a therapeutic substance.

23. A flexible scoring balloon catheter, comprising:

an inflatable elongate balloon having a distal end, a proximal end, and a working region therebetween configured for dilation within a vessel of a mammalian cardiovascular system vessel or other fluid or air carrying conduit or duct within a mammalian body, the balloon having a length along its working region, an outer surface along its working region, an internal passage along which a guide wire is insertable, and a first longitudinal axis centrally aligned with and extending through the internal passage, wherein the working region of the balloon in a folded or undeployed state respectively has a folded or undeployed outer cross sectional area perpendicular to the first longitudinal axis, and wherein the working region of the balloon in an expanded or deployed state respectively has an expanded or deployed outer cross sectional area perpendicular to the first longitudinal axis that is greater than the folded outer cross sectional area and the undeployed outer cross sectional area;

a catheter having a distal portion and a proximal portion, wherein the balloon is mounted on the catheter distal portion, and wherein the catheter comprises an inflation lumen extending therethrough in fluid communication with an interior region of the balloon; and a flexible elongate tubular spring structure of claim 1, surrounding portions of the working region of the balloon along the catheter distal portion.

24. The flexible scoring balloon catheter of claim 23, further comprising at least one of:

a tether structure configured for tethering or anchoring the tubular spring structure to at least one of a portion of the catheter and a portion of the balloon;

a proximal adhesive bond coupling a proximal end of the tubular spring structure to at least one of a proximal zone of the catheter distal portion and an unexpandable proximal segment of the balloon; and a distal adhesive bond coupling a distal end of the tubular spring structure to at least one of a distal zone of the catheter distal portion and an unexpandable distal segment of the balloon.

25. The flexible scoring balloon catheter of claim 24, wherein the tether structure comprises:

a tubular collar carried by a shaft of the catheter proximal to the balloon; and at least one elongate tether link coupled to each of the tubular collar and the tubular spring structure.

26. The flexible scoring balloon catheter of claim 24, wherein the flexible scoring balloon catheter includes each of the proximal adhesive bond and the distal adhesive bond, wherein the distal adhesive bond is intentionally formed to be weaker than the proximal adhesive bond.

27. The flexible scoring balloon catheter of claim 23, wherein the flexible scoring balloon catheter excludes protective elements configured to limit or shield contact between the plurality of scoring links and tissue within the vessel prior to inflation of the balloon from the folded, undeployed, or unexpanded state to the expanded or deployed state.

* * * * *